United States Patent [19]
Hawthorne et al.

[11] Patent Number: 6,074,625
[45] Date of Patent: Jun. 13, 2000

[54] BORON-CONTAINING HORMONE ANALOGS AND METHODS OF THEIR USE IN IMAGING OR KILLING CELLS HAVING HORMONE RECEPTORS

[75] Inventors: M. Frederick Hawthorne, Encino, Calif.; Mark T. Groudine, Seattle, Wash.

[73] Assignee: Neutron Therapies Inc., Seattle, Wash.

[21] Appl. No.: 08/808,203

[22] Filed: Feb. 28, 1997

Related U.S. Application Data

[63] Continuation of application No. 08/266,282, Jun. 27, 1994, abandoned.

[51] Int. Cl.$^7$ .......................... A61K 51/00; A61M 36/14
[52] U.S. Cl. .................. 424/1.11; 424/1.65; 424/1.61; 424/9.1
[58] Field of Search .................. 424/1.11, 1.33, 424/1.37, 1.61, 1.81, 9.1, 1.45, 1.65

[56] References Cited

U.S. PATENT DOCUMENTS

| | | |
|---|---|---|
| 3,995,060 | 11/1976 | Neri et al. . |
| 4,191,775 | 3/1980 | Glen . |
| 4,198,435 | 4/1980 | Richardson . |
| 4,206,234 | 6/1980 | Richardson . |
| 4,307,111 | 12/1981 | Crawley . |
| 4,310,523 | 1/1982 | Neumann . |
| 4,329,364 | 5/1982 | Neri et al. . |
| 4,386,080 | 5/1983 | Crossley et al. . |
| 4,466,952 | 8/1984 | Hadd . |
| 4,474,813 | 10/1984 | Neri et al. . |
| 4,623,660 | 11/1986 | Richardson . |
| 4,636,505 | 1/1987 | Tucker . |
| 4,732,912 | 3/1988 | Pilgrim et al. . |
| 4,803,227 | 2/1989 | Brandes et al. . |
| 4,839,155 | 6/1989 | McCague . |
| 4,904,661 | 2/1990 | Pilgrim et al. . |
| 4,921,941 | 5/1990 | Nagabhushan et al. . |
| 5,021,414 | 6/1991 | Pilgrim et al. . |
| 5,047,431 | 9/1991 | Schickaneder et al. . |
| 5,066,479 | 11/1991 | Hawthorne . |
| 5,192,525 | 3/1993 | Yang et al. . |
| 5,219,548 | 6/1993 | Yang et al. . |
| 5,286,853 | 2/1994 | Spielvogel et al. . |
| 5,387,409 | 2/1995 | Nunn et al. . |
| 5,443,813 | 8/1995 | Hainfield . |
| 5,630,786 | 5/1997 | Griffin et al. ............................ 600/3 |

FOREIGN PATENT DOCUMENTS

| | | |
|---|---|---|
| 0 253 503 B1 | 12/1991 | European Pat. Off. . |
| WO93/09771 | 3/1993 | WIPO . |

OTHER PUBLICATIONS

Kane et al (1993), J. Am. Chem. Soc., vol. 115, pp. 8853–8854, Automated Synthesis of Carborane–derived Homogenous Oligophosphates: Reagents for use in the Immunoprotein Mediated Boron Capture Therapy (BNCT) of Cancer.

Javid, M. et al., "The Possible Use of Neutron–Capturing Isotopes Such as Boron$^{10}$ in the Treatment of Neoplasms. II. Computation of the Radiation Energies and Estimates of Effects in Normal and Neoplastic Brain," *J. Clin. Invest.*, 31:604–610 (1952).

Sweet, W.H., "The Uses of Nuclear Disintegration in the Diagnosis and Treatment of Brain Tumor," *N. Engl. J. Med.*, 245(23):875–878(1951).

Sweet, W.H. and Javid, M., "The Possible Use of Neutron–Capturing Isotopes Such as Boron$^{10}$ in the Treatment of Neoplasms. 1. Intracranial Tumors," *J. Neurosurg.*, 9:200–209 (1952).

Farr, L.E. et al., "Neutron Capture Therapy With Boron in the Treatment of Glioblastoma Multiforme," *Am. J. Roentgenol.*, 71(2):279–293 (1954).

Godwin, J.T. et al., "Pathological Study of Eight Patients With Glioblastoma Multiforme Treated by Neutron–Capture Therapy Using Boron 10," *Cancer*, 8:601–615 (1955).

Hatanaka, H., *Boron–Neutron Capture Therapy for Tumors*, H. Hatanaka, Ed., Nishimura Co. Ltd., Nigata, Japan, p. 5 (1986).

Goldenberg, D. et al., "Neutron–capture Therapy of Human Cancer: In vivo Results on Tumor Localization of Boron–10–Labeled Antibodies to Carcinoembryonic Antigen in the GW–39 Tumor Model System," *Proc. Nat'l Acad. Sci.*, 81:560–563 (1984).

Hartman et al (Apr. 1994), Radiotherapy and Oncology, vol. 31, No. 1, pp. 61–75, "Radiation does heterogeneity in receptor and antigen mediated boron neutron capture therapy".

Barth, R.F. et al., "Conjugation, Purification and Characterization of Boronated Monoclonal Antibodies For Use In Neutron Capture Therapy," *Strahlenther. Onkol.*, 165(2/3):142–145 (1989).

(List continued on next page.)

*Primary Examiner*—Jose' G. Dees
*Assistant Examiner*—Dameron Jones
*Attorney, Agent, or Firm*—Christensen O'Connor Johnson & Kindness PLLC

[57] ABSTRACT

Boron containing compounds are targeted to hormonally responsive cells by contacting the cells with a conjugate of a boron containing moiety conjugated to a ligand having binding specificity for an intracellular receptor of the cell. The conjugates are useful for imaging or killing hormonally responsive cells, such as hormonally responsive tumor cells. For target cell killing, the cells are contacted with a $^{10}$B containing moiety conjugated to a ligand having binding specificity for an intracellular hormone receptor of the cells. The $^{10}$B containing moiety becomes associated with the hormone receptor of the cells, which may then be irradiated with neutrons to kill the cells by boron neutron capture. For target cell imaging, the cells are contacted with a $^{11}$B containing moiety conjugated to a ligand having binding specificity for an intracellular hormone receptor of the cells, and the boron that becomes associated with the hormone receptor of the cells may then be imaged using magnetic resonance imaging techniques.

23 Claims, 8 Drawing Sheets

OTHER PUBLICATIONS

Tamat, S. et al., "Boronated Monoclonal Antibodies for Potential Neutron Capture Therapy of Malignant Melanoma and Leukaemia," *Strahlenther. Onkol.*, 165(2/3):145–147 (1989).

Abraham, R. et al., "Boronated Antibodies for Neutron Capture Therapy," *Strahlenther. Onkol.*, 165(2/3):148–151 (1989).

Varadarajan, A. and Hawthorne, M.F., "Novel Carboranyl Amino Acids and Peptides: Reagents for Antibody Modification and Subsequent Neutron–Capture Studies," *Bioconjugate Chem.*, 2(4):242–253 (1991).

Paxton, R.J. et al., "Carboranyl Peptide–Antibody Conjugates for Neutron–Capture Therapy: Preparation, Characterization and In Vivo Evaluation," *Bioconjugate Chem.*, 3(3):241–247 (1992).

Shelly, K. et al., "Model Studies Directed Toward The Boron Neutron–Capture Therapy of Cancer: Boron Delivery To Murine Tumors With Liposomes," *Proc. Natl. Acad. Sci. USA*, 89:9039–9043 (1992).

Evans, R.M., "The Steroid and Thyroid Hormone Receptor Superfamily," *Science*, 240:889–895 (1988).

Pitochelli, A. et al., "The Isolation of the Icosahedral $B_{12}H_{12}^{-2}$ Ion," *J. Am. Chem. Soc.*, 82:3228 (1960).

Miller, H.C. and Miller, N.E., "Synthesis of Polyhedral Boranes," *J. Am. Chem. Soc.*, 85:3885–3886 (1963).

Hawthorne, M.F. and Pitochelli A.R., "The Reactions of Bis–Acetonitrile Decaborane with Amines," *J. Am. Chem. Soc.*, 81:5519 (1959).

Lipscomb, A. et al., "Probable Structure of the $B_{10}H_{10}^{-2}$ Ion," *J. Am. Chem. Soc.*, 81:5833 (1959).

Knoth, W. et al., "Chemistry of Boranes. XIX. Derivative Chemistry of $B_{10}H_{10}^{-2}$ and $B_{12}H_{12}^{-2}$," *J. Am. Chem. Soc.*, 86:3973–3983 (1964).

Tolpin E. et al., "Synthesis and Chemistry of Mercaptoundecahydro–closo–dodecaborate(2–)," *Inorg. Chem.*, 17(10):2867–2873 (1978).

Hawthorne, M.F., *Angewandte Chemie*, International Edition in English, 32(7):950–984 (1993).

Dunks, G. and Hawthorne, M.F., "The Non–Icosahedral Carboranes: Synthesis and Reactions," *Accts. Chem. Res.*, 6:124–131 (1973).

Grafstein, J. and Dvorak, J., "Neocarboranes, a New Family of Stable Organoboranes Isomeric with the Carboranes," *Inorg. Chem.*, 2(6):1126, 1129–1133 (1963).

Knoth, W.H., "1–$B_9H_9CH^-$ and $B_{11}H_{11}CH^-$," *J. Am. Chem. Soc.*, 89(5):1274–1275 (1967).

Morris, J. et al., "Preparations of New Boron Compounds with Potential for Application in $^{10}B$ NCT: Derivatives of Monocarbon Carboranes," In Proceedings of the Fourth International Symposium on Neutron Capture Therapy of Cancer in *Progress in Neutron Capture Therapy of Cancer*, B.J. Allen et al., Eds., Plenum Press, New York, NY, pp. 215–217 (1992).

Kane, R.R. et al., "Automated Syntheses of Carborane–Derived Homogeneous Oligophosphates: Reagents for Use in the Immuno–protein–Mediated Boron Neutron Capture Therapy of Cancer," *J. Am. Chem. Soc.*, 115(19):8853–8854 (1993).

Kane, R.R. et al., "Solution–Phase Synthesis of Boron–Rich Phosphates," *J. Org. Chem.*, 58(12):3227–3228 (1993).

Kane, R.R. et al., "Novel Carboranyl Diols and Their Derived Phosphate Esters," *Advances in Neutron Capture Therapy*, A.H. Soloway et al., Eds., Plenum Press, New York, NY, pp. 293–296 (1993).

Shelly, K. et al., "Model Studies Directed Toward the Boron Neutron–Capture Therapy of Cancer: Boron Delivery to Murine Tumors With Liposomes," *Proc. Natl. Acad. Sci. USA*, 89:9039–9043 (1992).

Kabalka, G.W. et al., "A New Boron MRI Method For Imaging BNCT Agents In Vivo," In *Progress in Neutron Capture Therapy for Cancer*, B.J. Allen et al., Eds., Plenum Press, New York, NY, pp. 321–323 (1992).

Bradshaw, K.M. et al., "In Vivo Pharmacokinetic Evaluation of Boron Compounds Using Magnetic Resonance Compounds in Spectroscopy and Imaging," In *Progress In Neutron Capture Therapy For Cancer*, B.J. Allen et al., Eds., Plenum Press, New York, NY, pp. 325–329 (1992).

Schilling, K. and Shutsung, L., "The Use of Radioactive 7α, 17α–Dimethyl–19–Nortestosterone (Mibolerone) in the Assay of Androgen Receptors," *The Prostate*, 5:581–588 (1984).

Traish, A.M. et al., "Binding of 7α, 17–α–Dimethyl–19–Nortestosterone (Mibolerone) to Androgen and Progesterone Receptors in Human and Animal Tissues," *Endocrinology* 118(4):1327–1333 (1986).

Neifeld, J.P., "The Potential of Hormone Receptors in the Treatment of Various Cancers," *Oncology*, 3(8):57–62 (1989).

Baker, J.W. et al., "Synthesis and Bacteriostatic Activity of Some Nitrotrifluoromethylanilides," *J. Med. Chem.*, 10:93–95 (1967).

BORON-CONTAINING HORMONE ANALOGS AND METHODS OF THEIR USE IN IMAGING OR KILLING CELLS HAVING HORMONE RECEPTORS

This application is a continuation of application Ser. No. 08/266,282, field Jun. 27, 1994 now abandoned.

FIELD OF THE INVENTION

The present invention relates to new agents for use in boron imaging and neutron capture therapy. More particularly, this invention relates to boron neutron capture or imaging agents in which a boron containing moiety is conjugated to a ligand having binding specificity for a hormone receptor of a cell.

BACKGROUND OF THE INVENTION

The development of quantum mechanics, nuclear physics and associated chemistry which occurred in the 1930's led James Chadwick (*Nature* 129:312, 1932) to the discovery of the neutron in 1932. Studies of the interactions of neutrons with a variety of materials uncovered the phenomenon of neutron scattering by elastic collisions (J. R. Dunning et al., *Phys. Rev.* 47:325, 1935) with atomic nuclei, especially the proton of the H-atom. Capture of slow (or thermal energy) neutrons by certain nuclei was disclosed in Fermi et al., *Proc. Roy. Soc. London,* 146:483 (1934) and the disintegration of other specific nuclei by interaction with thermal neutrons was disclosed in J. R. Dunning et al., *Phys. Rev.,* 48:265 (1935). By 1935 a mass of experimental information had been collected, from which it was apparent that the ability of an atomic nucleus to capture a neutron was related not to the mass of the target nucleus, but to the actual structure of that nucleus. The concept of nuclei having a characteristic effective cross-sectional area, expressed as units of $10^{-24}$ cm$^2$ known as barn units, was introduced with this early work. The effective nuclear cross section of boron for neutron capture was known to be exceptionally large while boron's neighbors in the periodic table, nitrogen and carbon, exhibited nuclear cross sections which were comparatively quite small.

Taylor, *Proc. Roy. Soc.,* A47:873 (1935) described the capture of thermal neutrons by $^{10}$B nuclei followed by the production of $^4$He$^{2+}$($\alpha$-particles) and $^7$Li$^{3+}$ with about 2 MeV of kinetic energy distributed between these two heavy ion products. It was also determined (Taylor, supra) that the translational range of the product ions was particularly short; about 7.6 $\mu$in photographic gelatin and 1.1 cm in air. Consequently, the lithium ion and the $\alpha$-particle products were short-lived, energetic species capable of imparting immense local damage to organic materials through ionization processes.

Gordon L. Locher of the Bartol Research Foundation of the Franklin Institute in Philadelphia, Pa. noted the potential medical applications of neutrons and boron neutron capture, in *Am. J. Roentgenol. and Radium Therapy,* 36:1 (1936). Locher's concept invoked the simple boron neutron capture reaction as the basis of a binary therapeutic method wherein a $^{10}$B nucleus contained in a compound which specifically localizes in tumor reacts with a thermal neutron to produce the energetic cytotoxic reaction products, an $\alpha$-particle and a lithium ion. In this process no radioactive materials are involved and the therapeutic process may be modulated by controlling the supply of neutrons to the tumor site.

The two necessary components of the boron neutron capture (BNC) process, a controllable source of low-energy neutrons with a usefully high flux and suitable boron compounds for tumor localization were unknown in 1936 and Locher's concept remained prophetic until nuclear reactors were available to support an initial experimental test using thermal neutrons. This initial event did not occur until 1954 when Sweet, Farr and their coworkers (M. Javid et al., *J Clin. Invest.,* 31:603 (1952); W. H. Sweet, *N. EngL. J. Med.,* 245:875 (1951); W. H. Sweet and M. Javid, *J. Neurosurg.,* 9:200 (1952); L. E. Farretal., *Am. J. Roentgenol,* 71:279 (1954); J. T. Godwin et al., *Cancer,* 8:601 (1955)) treated human brain tumors (glioblastoma multiforme) using $^{10}$B-enriched borate as the $^{10}$B target species in terminal patients. In these first experiments, BNCT was applied to the problem of killing malignant glioma cells which remained at the tumor site following normal surgical procedures.

The boron neutron capture (BNC) reaction obtained with thermal, 293K (0.025 eV), neutrons may be represented as shown in Equation (1):

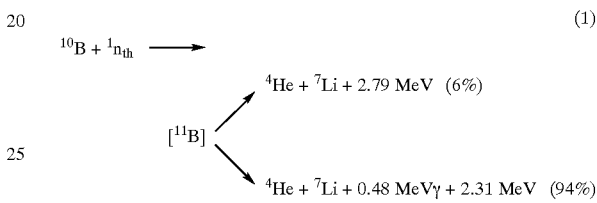

(1)

The $^{11}$B nucleus is incapable of undergoing a BNC reaction while the effective nuclear cross section of $^{10}$B is 3837 barns.

Two other nuclides, $^1$H and $^{14}$N, are abundant in tissue and participate in important neutron capture side-reactions which occur during BNCT and thus contribute important doses of background radiation to the subject. These two neutron capture reactions play a role, not because of enhanced nuclear cross sections of the target nuclei, but due to their very high concentrations in tissue. As disclosed in H. Hatanaka, *Boron-Neutron Capture Therapy for Tumors* (H. Hatanaka, Ed.), Nichamura Co. Ltd., Nigata, Japan, p. 5 (1986), the neutron capture reactons of $^1$H and $^{14}$N are as shown in Equations (2a) and (2b), respectively:

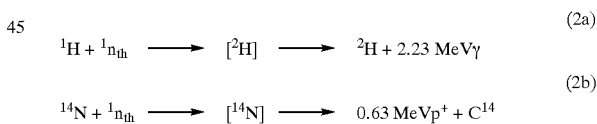

The passage of a neutron through hydrogen-rich media, such as tissue, results in the slowing and scattering of these neutrons by collisions with nuclear protons of the H-atoms. Occasionally, a slowly moving neutron will be captured by such a proton and produce a deuteron accompanied by characteristic gamma radiation which contributes to the total radiation dose. In another competing capture reaction, the nitrogen atoms available in tissue may capture a low-energy neutron and generate $^{14}$C and an 0.63 MeV (kinetic energy) proton. The kinetic energy imparted to the $^7$Li$^{3+}$ and $^4$He$^{2+}$ ions derived from the BNC reaction and that similarly associated with the proton and $\gamma$-photons, produced as shown in (2a) and (2b), is transferred to the surrounding media. Since all of these energetic nuclear reaction products, with the exception of the $\gamma$-photons, are heavy particles, this kinetic energy transfer is rapid and takes place along a very short path length. The rate of linear energy transfer, LET, of these particles is characteristically high and the immense energy of these reactions is therefore deposited in a very small volume. As an example, the $^7Li^{3+}$ and $^4He^{2+}$ ions generated in the BNC reaction generate ionization tracks about 0.01 mm long or the equivalent of approximately one cell diameter. Thus, the high LET characteristic of particles produced by nuclear reactions which occur within tissue are especially lethal to affected cells due to the high density of deposited energy.

Ideally, those cells which carry large numbers of $^{10}B$ nuclei are subject to destruction by BNC while neighboring cells that are free of $^{10}B$ are spared, save for the contribution of the background $^1H(n,\gamma)^2H$ and $^{14}N(n,p)^{14}C$ reactions. In order for the delivery of $^{10}B$ to tumor cells to achieve this desired effect in BNCT the selectivity of boron delivery to tumor versus normal tissue, which is subject to neutron irradiation, should be as great as possible. In addition, the actual concentration of $^{10}B$ in tumor must be sufficiently high to offer a localized binary therapeutic effect well above the background radiation dose delivered by the $^1H(n,\gamma)^2H$ and $^{14}N(n,p)^{14}C$ neutron capture processes shown above. The minimum generally accepted $^{10}B$ concentration necessary for effective BNC has been commonly believed to be between 10 and 30 μg $^{10}B$/g tumor depending upon the precise location of the $^{10}B$ with respect to vital components of the tumor cell structure. As the position of the $^{10}B$ nuclei is changed from the external cell wall to the cytoplasm to the nucleus of the cell, the required concentration of $^{10}B$ for effective BNCT decreases, as expected. Thus, cell wall-bound $^{10}B$ might require 30 ppm or greater concentrations while $^{10}B$ localized within the nucleus of the tumor cell might only require a concentration of 10 ppm or less. An additional factor is the steady state concentration of thermal neutrons in the targeted volume of tissue since very low neutron intensities require proportionally longer irradiation times to produce the required number of BNC events for effective therapy.

Due to the necessity of attaining base levels of tumor cell associated boron, attempts have previously been made to enhance the delivery of boron to tumor cells to obtain sufficiently high concentrations of boron in the cells for effective boron neutron capture therapy, while leaving relatively low amounts of background boron that can result in bystander cell or tissue damage upon neutron irradiation. For example, some tumor cell targeting strategies have employed the use of boron compounds with some natural affinity for tumors, such as 4-(dihydroxyboryl) phenlyalanine (BPA) or the mercaptoundecahydro-closo-dodecaborate dianion ($B_{12}H_{11}SH^{2-}$; BSH), or the attachment of boron-containing species to other molecules such as porphyrins. In addition, it has previously been proposed to conjugate $^{10}B$ enriched boron to antibodies specific for tumor associated antigens to enhance the therapeutic effectiveness of BNC therapy. See, for example, D. Goldenberg et al., "Neutron-capture Therapy of Human Cancer: In vivo Results on Tumor Localization of Boron-10-Labeled Antibodies to Carcinoembryonic Antigen in the GW-39 Tumor Model System," *Proc. Nat'l Acad. Sci.* 81:560–563 (1 984); R. Barth et al., "Conjugation, Purification and Characterization of Boronated Monoclonal Antibodies For Use In Neutron Capture Therapy," *Strahlenther. Onkol.* 165(2/3): 142–145 (1989); S. Tamat et al., "Boronated Monoclonal Antibodies for Potential Neutron Capture Therapy of Malignant Melanoma and Leukemia," *Strahlenther. Onkol.* 165 (2/3):145–147 (1989); R. Abraham et al., "Boronated Antibodies for Neutron Capture Therapy," *Strahlenther. Onkol.* 165(2/3):148–151 (1989); A. Varadarajan et al., "Novel Carboranyl Amino Acids and Peptides: Reagents for Antibody Modification and Subsequent Neutron-Capture Studies," *Bioconjugate Chem.* 2(4):242–253 (1991); and R. Paxton et al., "Carboranyl Peptide-Antibody Conjugates for Neutron-Capture Therapy: Preparation, Characterization, and In Vivo Evaluation," *Bioconjugate Chem.* 3(3):241–247 (1991). Alternatively, it has been proposed to incorporate boron agents into liposome vesicles to provide an extended circulation lifetime for the agents, to protect the agents from attack by normal physiological agents and to reduce potential toxic side-effects. Certain liposomes also target specifically to neoplastic tissues. See, e.g., "Model Studies Directed Toward The Boron Neutron-Capture Therapy of Cancer: Boron Delivery To Murine Tumors With Liposomes," *Proc. Natl. Acad. Sci. USA*, 89:9039–9043 (1993).

Despite the advances that have been made in boron delivery methodology, the problems of low circulation lifetime, relatively low tumor specificity, less than optimal liposome composition, potentially toxic side effects and/or less than optimal cell membrane interactions have prevented these methods from achieving the highly specific delivery of boron to target tumor cells in therapeutically desirable concentrations. Thus, a strong need exists in the art for new and improved vehicles for the delivery of boron to target tumor cells for boron neutron capture therapy and imaging purposes.

It is also known that certain hormones bind to and activate specific intracellular receptors to alter the pattern of gene activity within cells. In the hormonal regulation of gene activity, a ligand (which can be a hormone or a synthetic analog) moves into a cell by facilitated diffusion. Once inside the cell, the ligand binds to its intracellular receptor to form a ligand/intracellular receptor complex that induces a change in the shape of the receptor and activates the receptor to carry out other functions within the cell. It is generally believed that the ligand/intracellular receptor complex recognizes and binds to specific short sequences of DNA within the control region of hormone-responsive genes, thereby mediating gene activity. Although much remains to be learned about the specifics of such mechanisms, it is known that exogenous inducers such as hormones modulate gene transcription by acting in concert with intracellular components, including intracellular receptors and discrete DNA known as hormone response elements. More specifically, it is known that hormones like the glucocorticoid, sex and thyroid hormones enter cells by facilitated diffusion. It is also known that the hormones then bind to specific receptor proteins, thereby creating a hormone/receptor complex. The binding of hormone to the receptor is believed to initiate an alosteric alteration of the receptor protein. As a result of this alteration, it is believed that the hormone/receptor complex is capable of binding with high affinity to certain specific sites on the chromatin DNA. Such sites, which are referred to in the art by a variety of names, modulate expression (transcription of RNA) of nearby target gene promoters. Unlike protein or peptide therapeutics, natural and synthetic ligands for intracellular receptors are small organic molecules sharing many of the attractive properties of pharmaceutical drugs, including suitability for oral or topical administration. The receptors for the non-peptide hormones are closely related members of a superfamily of proteins. This protein superfamily of receptors has been called intracellular receptors because the receptors are located inside target cells, unlike the receptors for neurotransmitters and protein or peptide hormones and growth factors, which are located in the plasma membranes of cells.

SUMMARY OF THE INVENTION

It has now been discovered that boron containing compounds can be targeted to hormonally responsive cells having at least one type of intracellular hormone receptor by contacting the cells with a boron containing agent comprising a boron containing moiety conjugated to a ligand having binding specificity for an intracellular receptor of the cell. In a presently particularly preferred embodiment, the methods of the invention are useful for killing hormonally responsive cells, such as hormonally responsive tumor cells, and are carried out by contacting the cells with a boron neutron capture agent comprising a $^{10}B$ containing moiety conjugated to a ligand having binding specificity for an intracellular hormone receptor of the cells. The $^{10}B$ containing moiety becomes associated with the hormone receptor of the cells, which may then be irradiated with neutrons to kill the cells by boron neutron capture. In order to avoid cell activation outside of the irradiation target areas, ligands of the invention are preferably antireceptor agents or antagonists that bind to the intracellular receptors but fail to the activate the intracellular receptors, and that block activation of the receptors by subsequent exposure to the receptors' natural hormones. In alternative embodiments, target cells may be contacted with a boron containing conjugate of the invention to associate boron with the target cells, and then the target cells may be imaged using, for example, magnetic resonance imaging techniques.

In representative embodiments of this aspect of the invention, the target cells may comprise, for example, metastatic breast cancer cells and the boron neutron capture agent may comprise a $^{10}B$ containing moiety conjugated to ligand, such as a tamoxifen residue or analog, having binding specificity for estrogen receptors. In other representative embodiments, the target cells may comprise, for example, prostate cancer cells and the boron neutron capture agent may comprise a $^{10}B$ containing moiety conjugated to ligand, such as a 4'- substituted or a 3',4'-disubstituted anilide residue, having binding specificity for androgen receptors. In yet further representative embodiments, the target may comprise, for example leukemia cells and the boron neutron capture agent may comprise a $^{10}B$ containing moiety conjugated to ligand having binding specificity for glucocorticoid receptors; the target may comprise renal carcinoma cells and the boron neutron capture agent may comprise a $^{10}B$ containing moiety conjugated to ligand having binding specificity for progesterone receptors, androgen receptors or glucocorticoid receptors; the target cells may comprise endometrial cancer cells and the boron neutron capture agent may comprise a $^{10}B$ containing moiety conjugated to ligand having binding specificity for estrogen receptors or progesterone receptors; the target cells may comprise ovarian carcinoma cells and the boron neutron capture agent may comprise a $^{10}B$ containing moiety conjugated to ligand having binding specificity for estrogen receptors or progesterone receptors; or the target cells may comprise carcinoma cells of the cervix, vagina or vulva and boron neutron capture agent may comprise a $^{10}B$ containing moiety conjugated to ligand having binding specificity for estrogen receptors or progesterone receptors.

In other aspects of the invention, novel compounds are provided which comprise a $^{10}B$ containing moiety conjugated to a ligand having binding specificity for an intracellular receptor of a target cell. Representative embodiments of the compounds of the invention include conjugates having ligands exhibiting binding specificity for glucocorticoid and mineralocorticoid receptors; the sex steroid receptors, such as progesterone, estrogen, estrogen-related, and androgen receptors; as well as vitamin D3, thyroid, and retinoic acid receptors. The $^{10}B$ containing moiety of the conjugates of the invention may comprise a single boron atom, such as boric acid, but preferably comprise more than one $^{10}B$ atom, more preferably at least nine $^{10}B$ atoms and most preferably at least eighteen $^{10}B$ atoms. Suitable boron neutron capture agents may be based on polyhedral borane anion derivatives, such as closo-$B_{12}H_{12}^{2-}$; closo-$B_{10}H_{10}^{2-}$ or BSH ($B_{12}H_{12}SH^{2-}$), on derivatives that comprise two polyhedral borane anion cages linked together to form a structure comprising 20 boron atoms, on polyhedral carboranes such as compounds of the formulas closo-$C_2B_{n-2}H_n$, or closo-$CB_{n-1}H_n$, on oligomeric peptides constructed from boron-rich α-amino acids, or on boron-rich oligophosphates. Illustrative compounds of the invention may be generally represented by the formula:

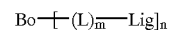

wherein Bo is a boron containing moiety, L is a linking group, Lig is a ligand, m is 0 or 1, and n is an integer greater than or equal to 1, or a pharmaceutically acceptable salt thereof.

BRIEF DESCRIPTION OF THE DRAWINGS

The foregoing aspects and other advantages of this invention will become more readily appreciated by reference to the following detailed description and accompanying drawings, wherein.

DETAILED DESCRIPTION OF THE PREFERRED EMBODIMENT

Figure 1A:
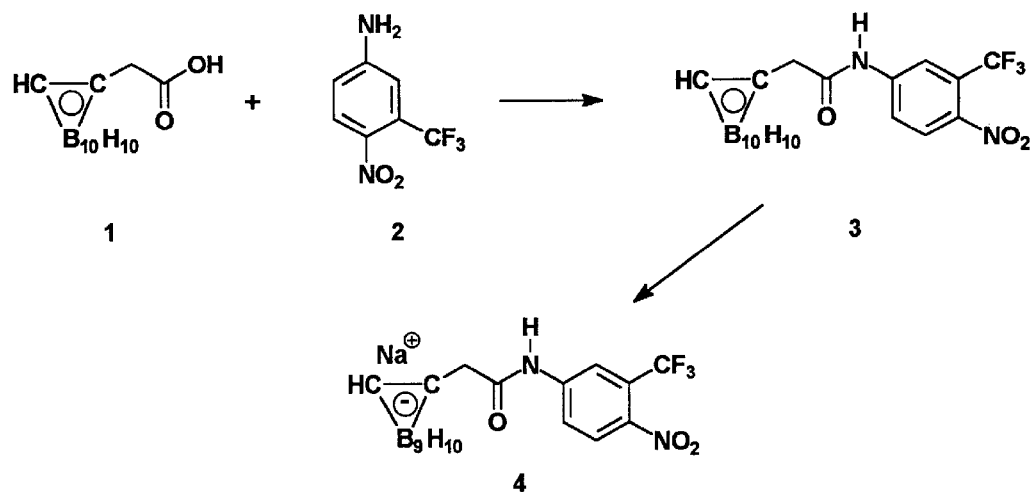
FIG. 1A is a schematic representation of the synthesis pathway for the synthesis of the nido-carboranyl flutamine derivative N-(2'-nido-carboranylacetyl)-3-trifluoromethyl-4-nitroaniline 4, as described in Examples 1 and 2.

In accordance with the present invention, boron is targeted to intracellular receptor containing cells by contacting the cells with a conjugate comprising a boron containing moiety conjugated to a ligand having binding specificity for at least one type of intracellular receptor of the cells.

As used in the present application, "intracellular receptor containing cells" is intended to mean cells that contain one or more intracellular receptors for natural or synthetic hormones or hormone analogs. In presently particularly preferred embodiments, the receptors may be selected from the steroid hormone superfamily of receptors, including the adrenal steroid receptors, such as glucocorticoid and mineralocorticoid receptors; the sex steroid receptors, such as progesterone, estrogen, estrogen-related, and androgen receptors; as well as vitamin D3, thyroid, and retinoic acid receptors. See, for example, Evans et al., *Science* 240:889 et seq. (1988).

The boron containing agents of the invention comprise a boron containing moiety conjugated to a ligand having binding specificity for an intracellular receptor of the cell. Thus, the agents of the invention can generally be represented by the formula:

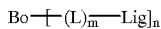

wherein Bo is a boron containing moiety, L is a linking group, Lig is a ligand, m is 0 or 1, and n is an integer greater than or equal to 1.

As used herein, the term boron containing moiety means the residue of a boron compound after reaction with a ligand to form a conjugate of the invention. Suitable boron compounds useful in the practice of the invention include compounds comprising a single boron atom per molecule, such as boric acid, as well as compounds containing more than one boron atom per molecule. For example, the boron compounds may be based on polyhedral borane anion derivatives, such as closo-$B_{12}H_{12}{}^{2-}$(Pitochelli, A. et al., *J. Am. Chem. Soc.* 82:3228 et seq. (1960); Miller, H., *J. Am. Chem. Soc.* 85:3885 et seq. (1963)), or closo-$B_{10}H_{10}{}^{2-}$ (Hawthorne, M. F. et al., *J. Am. Chem. Soc.* 81:5519 et seq. (1959); Lipscomb, A., *J. Am. Chem. Soc.* 81:5833 et seq. (1959)). A representative, presently particularly preferred polyhedral borane anion derivative of this class includes BSH ($B_{12}H_{12}SH^{2-}$; Knoth, W., *J. Am. Chem. Soc.* 86:3973 et seq. (1964); Tolpin, E. et al., *Inorg. Chem.* 17:2867 (1978)) that contains a thiol function to permit covalent disulfide bonds with thiol groups presented by serum and tumor proteins.

Alternatively, the boron compounds of the invention may comprise two polyhedral borane anion cages linked together to form a linked cage structure comprising, for example 20 boron atoms (hereinafter referred to as "$B_{20}$ compounds"; see M. F. Hawthorne, *Angewandte Chemie, International Edition in English*, 32:950–984 (1993)). $B_{20}$ compounds of the invention may be represented by the general formulas:

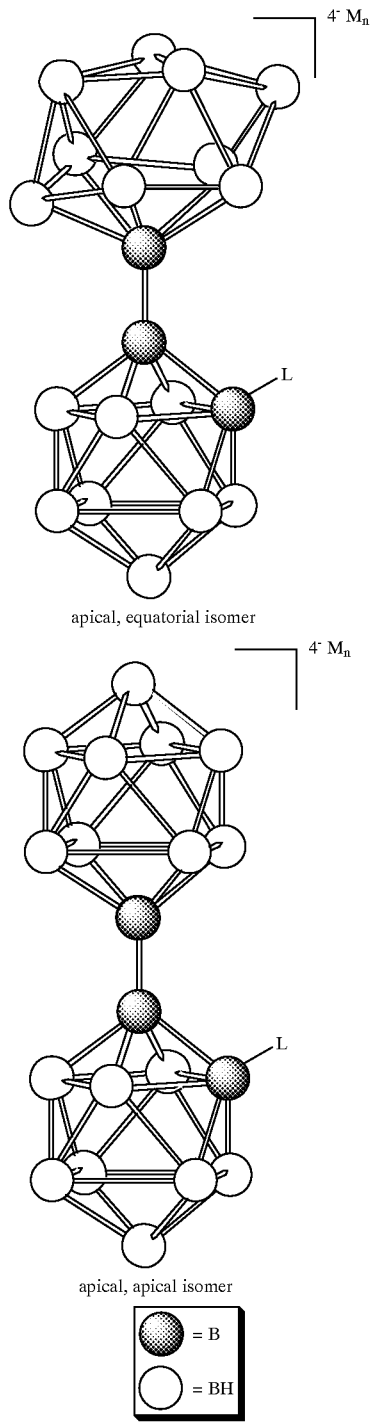

apical, equatorial isomer apical, apical isomer as well as derivatives thereof, and include compounds of the formula $M_nB_{20}H_{17}L$, wherein M is a cation, e.g., an alkali metal or tetra alkyl ammonium cation, n is and integer from 1 to 4, and L is a two electron donor. Preferably, M is Na, K, Cs or Rb, and alkyl includes methyl, ethyl and other alkyls which do not render the resulting salt insoluble. L is a two electron donor, preferably selected from the group consisting of —NHR₁R₂ wherein R₁ and R₂ are the same or different and are selected from the group consisting of hydrogen, benzyl, alkyl and diamine (e.g., ethylene diamine); and —SR₁R₂ wherein R₁ is selected from the group consisting of hydrogen, benzyl, alkyl and diamine, and R₂ is selected from the group consisting of hydrogen, alkyl, —XCN, —XCO, —XNCO, —XCO₂OH, —XCO₂OR, —XNHCONHR₁, —XCOOH, and —XCONHR₁, where X is alkyl or arylakyl having from 1 to 20 carbon atoms. Preferably, L is selected from the group consisting of —NH₃, —NH₂—CH₂—Ph, —NH₂CH₂CH₂NH₂ and —NH₂(CH₂)₇CH₃. Most preferably, L is —NH₃.

The boron compounds may also be based on polyhedral carboranes such as compounds of the formulas closo-$C_2B_{n-2}H_n$ (Dunks, G. et al., *Accts. Chem. Res.* 6:124 et seq. (1973); Grafstein, J., *Inorg. Chem.* 2:1128 et seq. (1963)), or closo-$CB_{n-1}H_n^-$(Knoth, W., *J. Am. Chem. Soc.* 89:1274 et seq. (1967); Morris, J. et al., *Proceedings of the Fourth International Symposium on Neutron Capture Therapy of Cancer in Progress in Neutron Capture Therapy of Cancer,* B. Allen et al., Ed., Plenum Press, New York, pp. 215 et seq. (1992)), as well as their corresponding nido-derivatives, e.g., compounds of the formula nido-$C_2B_{n-3}H_n^-$. The o-closo-$C_2B_{10}H_{12}$ carboranes are generally represented by the structures:

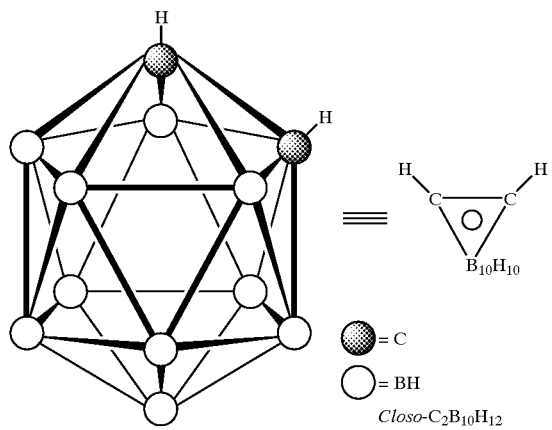

Closo-$C_2B_{10}H_{12}$ including derivatives thereof, while the corresponding anionic o-nido-$C_2B_9H_{12}^-$ carboranes and their derivatives may be represented as:

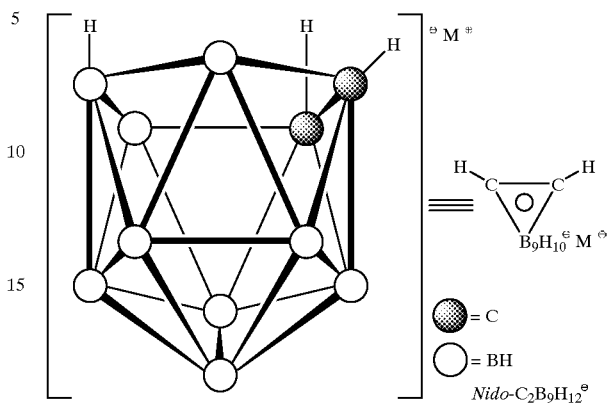

Nido-$C_2B_9H_{12}^\ominus$ where M⊕ represents a cation, such as an alkali metal cation or tetra alkyl ammonium cation.

More preferably, the boron compounds of the invention may comprise a plurality of carborane cage structures, such as oligomeric peptides constructed from boron-rich α-amnino acids using Merrifield solid phase synthesis methods as disclosed in Varadarajan, M. et al., *Bioconj. Chem.* 2:242 (1991) and Paxton, R. et al., *Bioconj. Chem.* 3:243 (1992), the disclosures of which are incorporated herein by reference. Even more preferably, the boron containing agents of the invention may comprise carborane-derived oligophosphates, such as those described in Kane, R. et al., "Automated Syntheses of Carborane-Derived Homogeneous Oligophosphates: Reagents for Use in the Immunoprotein-Mediated Boron Neutron Capture Therapy of Cancer," *J. Am. Chem. Soc.* 115(19):8853–8854 (1993); Kane, R. et al., "Solution-Phase Synthesis of Boron-Rich Phosphates," *J. Org. Chem.* 58(12):3227–3228 (1993); and R. Kane et al., "Novel Carboranyl Diols and Their Derived Phosphate Esters," *Advances in Neutron Capture Therapy,* A. H. Soloway et al., Eds., Plenum Press, New York (1993), the disclosures of which are incorporated herein by this reference. Representative compounds of this class include compounds of the formula:

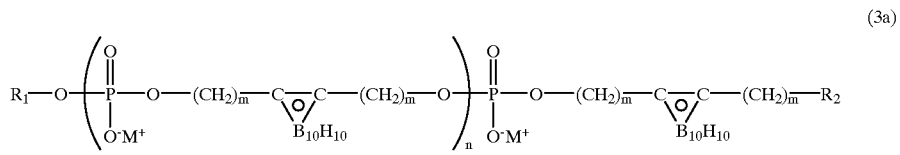

(3a)

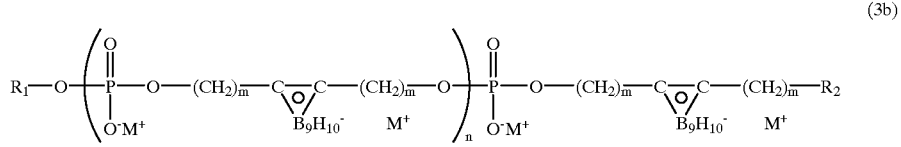

(3b)

wherein M⁺ is an alkali metal cation or tetra alkyl ammonium, as defined above, $R_1$ and $R_2$ are independently selected from groups suitable for linking to a ligand, targeting moieties and other functional groups for conveying desireable properties to the compounds, m is an integer from 1 to 10 and n is an integer from 2 to 150, preferably from 20 to 100. As used above, the group

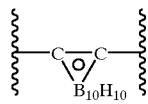

is intended to represent a carboranyl cage structure having a structural configuration as follows:

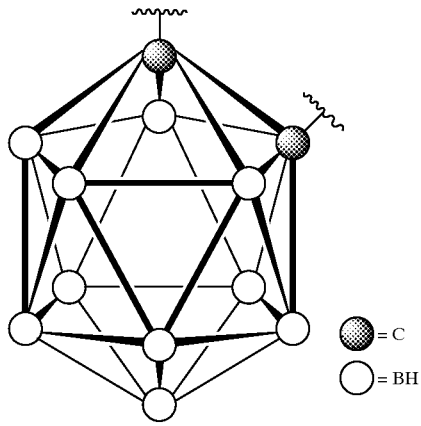

The isotopic content of the boron employed in the agents of the present invention can range from the natural abundance of approximately 19.78% $^{10}B$ up to an enriched population of 95% or more of $^{10}B$. When used for boron neutron capture therapy, use of material highly enriched in $^{10}B$ is preferred.

Ligands suitable for conjugation to the boron containing compounds include non-peptide small organic molecule compounds capable of specifically binding to the target intracellular receptors of the invention. Naturally occuring hormones or agonists of naturally occuring hormones bind to the target intracellular receptors and induce shape and function changes in the intracellular receptors. Although pure agonists, such as estrogen and progesterone, specifically bind to their corresponding receptors, use of pure agonists in the practice of the invention may result in stimulation of growth of certain tumor cells, whether inside or outside of the tissue area targeted for neutron radiation. Since tumor cells outside the neutron radiation target areas would not be subject to boron neutron capture cell killing, the use of pure agonists in the practice of the invention may, in some cases, result in the stimulation of tumor growth at remote sites. Accordingly, ligands of the invention are preferably antireceptor agents or antagonists that bind to the intracellular receptors, but fail to the activate the intracellular receptors and block activation of the receptors by subsequent exposure to the receptors' natural hormones. Antagonists for intracellular receptors are well known to those skilled in the art.

By way of illustration, when the target intracellular receptors are androgen receptors, representative ligands of the invention include antiandrogenic agents, such as the antiandrogenic N-phenyl amide derivatives disclosed in U.S. Pat. Nos. 3,995,060, 4,191,775, 4,329,364, 4,386,080, 4,636,505, 4,474,813, and 4,921,941, as well as EP Publication No. 0 253 503 B1, the disclosures of which are incorporated herein by this reference. A presently particularly preferred antiandrogenic agent for this purpose is 2-methyl-N-[4-nitro-3-(trifluoromethyl)-phenyl]propanamide, also known as flutamide. As a further illustrative example of an embodiment of the invention where the ligand is a flutamide residue, the boron containing compounds of the invention having binding specificity for androgen receptors include compounds of the formula:

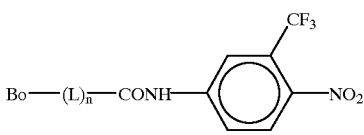

wherein Bo is a $^{10}$boron containing moiety, L is a linking group and n is 0 or 1, or the pharmaceutically acceptable salts thereof.

As a further illustrative example, when the target intracellular receptors are estrogen receptors, representative ligands of the invention include antiestrogen agents, such as the antiestrogenic triphenylalkene derivatives disclosed in U.S. Pat. Nos. 4,198,435, 4,206,234, 4,307,111, 4,310,523, 4,623,660, 4,839,155, 5,047,431, 5,192,525 and 5,219,548, the disclosures of which are incorporated herein by this reference. Presently particularly preferred antiestrogen ligands of this type include, for example, 1-(p-β-dimethylaminoethoxyphenyl)-trans-1,2-diphenyl-2-phenyl-but-1-ene, also known as tamoxifen; 1-[2-[p-(3,4-dihydro-6-methoxy-2-phenyl-1-naphthyl)-phenoxy]-ethyl]-pyrrolidine, also know as nafoxidine; and 2-[p-(2-chloro-1,2-diphenylvinyl)phenoxy]-triethylamine, also know as clomiphene, or the pharmaceutically acceptable salts thereof In addition to androgen and estrogen antagonists as described above, suitable ligand include antagonists for the adrenal steroid receptors, such as glucocorticoid and mineralocorticoid receptors, vitamin D3 receptors, thyroid receptors, and retinoic acid receptors, as will be apparent to those skilled in the art.

The boron containing agents of the present invention can be adrministered either as free agents or in connection with other delivery vehicles, such as unilamellar or multilamellar vesicles, including liposomes. The preparation and use of vesicles in drug delivery applications are well known and documented in the art. See, e.g., Shelly, K. et al., PNAS 89:9039 et seq. (1992), the disclosure of which is incorporated herein by this reference. In one embodiment of the invention, liposome encapsulated tumor treating agents of the invention may include a unilamellar or multilamellar liposome where the liposome comprises at least one encapsulating bilayer and an internal space defined by the encapsulating bilayer. A boron containing agent of the invention may then be encapsulated within the internal space or between the layers of the liposome. A wide variety of lipid particles may form delivery vesicles which are useful in this aspect of the invention. For example, phospholipid lipid vesicles such as those disclosed in EP patent application EP 0272091, the disclosure of which is incorporated herein by this reference, may be employed with the boron containing agents of the present invention. These phospholipid vesicles are composed of a single encapsulating phospholipid membrane associated with an amphiphile-associated substrate. Liposomes of this type may be prepared by methods conventional in the art. For example, a hydrated phospholipid suspension, when agitated, forms multilamellar vesicles, with water separating many bilayers having diameters of 1–10 μm. Application of a shearing or homogenizing force such as sonication to a multilamellar suspension produces small unilamellar vesicles of a size that may range from about 30 to about 250 nm, and more preferably from about 50 to about 100 nm in average diameter. This range is considered to be preferable to obtain optimal circulation time in vivo and target cell specificity. As used herein, "unilamellar" is generally meant to include from one to three, and preferably one, bilayer. The average diameter of the liposome encapsulated borane containing agents of the invention is dependent on many factors, including the sonication time of the phospholipid suspension, the composition of lipid materials employed, the methods by which the liposome is prepared and other relevant factors. Liposomes comprising boron containing agents of the invention embedded in the bilayer of the liposomes can be obtained by the methods disclosed in M. F. Hawthorne, *Angewandte Chemie, International Edition in English,* 32:950–984 (1993). For example, a dried film may be prepared by dissolving a lipophilic boron containing agent of the invention and a cholesterol:phospholipid mixture in chloroform, and then removing the solvent in vacuo. The resulting dry film is then homogenized by sonication, and the resulting vesicles are separated from free boron containing agent, such as by eluting through a column of Sephadex G-25 (medium) with isotonic phosphate-buffered saline or lactose. The amount of boron embedded in the liposome bilayer is dependent on the amount of boron containing agent added to the original mixture, and can be controlled as desired.

The boron containing agents of the invention may be employed in vitro or in vivo for killing or imaging of target cells containing intracellular receptors. For the boron neutron capture killing of target cells, the cells are contacted with at least one boron containing agent of the invention, and then the cells are subjected to neutron bombardment from a source that emits thermal, epithermal or fast neutrons, as is known by those skilled in the art. For in vivo applications, compositions of boron containing agents of the invention generally comprise an amount of a boron effective, when administered to a human or other animal subject, to localize a sufficient amount of boron at target tissue sites to enable subsequent neutron irradiation, boron neutron capture and target cell killing, or to enable imaging of the target tissue, together with a pharmaceutically acceptable carrier. Any pharmaceutically acceptable carrier may be generally used for this purpose, provided that the carrier does not significantly interfere with the stability or bioavailability of the boron containing agents of the invention.

For boron imaging of target cells, the cells are similarly contacted with at least one boron containing agent of the invention and the cells or tissues are imaged using magnetic resonance imaging techniques, such as those described in Kabalka, G. W. et al., "A New Boron MRI Method For Imaging BNCT Agents In Vivo," in *Progress In Neutron Capture Therapy For Cancer,* B. J. Allen et al., Eds., Plenum Press, New York, N.Y. 1992, pp. 321–323; and Bradshaw, K. H. et al., "In Vivo Pharmacokinetic Evaluation of Boron Compounds Using Magnetic Resonance Compounds in Spectorscopy and Imaging," in *Progress In Neutron Capture Therapy For Cancer,* B. J. Allen et al., Eds., Plenum Press, New York, N.Y. 1992, pp. 325–329.

The boron containing agent compositions can be administered in any effective pharmaceutically acceptable form to warm blooded animals, including human and other animal subjects, e.g., in topical, lavage, oral, suppository, parenteral, or infusable dosage forms, as a topical, buccal, or nasal spray or in any other manner effective to deliver the boron containing agents to a site of target cells. The route of administration will preferably be designed to optimize delivery and localization of the agents to the target cells.

For topical applications, the pharmaceutically acceptable carrier may take the form of liquids, creams, lotions, or gels, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration.

Compositions designed for injection may comprise pharmaceutically acceptable sterile aqueous or nonaqueous solutions, suspensions or emulsions. Examples of suitable nonaqueous carriers, diluents, solvents, or vehicles include propylene glycol, polyethylene glycol, vegetable oils, such as olive oil, and injectable organic esters such as ethyl oleate. Such compositions may also comprise adjuvants such as preserving, wetting, emulsifying, and dispensing agents. They may be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

Solid dosage forms for oral or topical administration include capsules, tablets, pills, suppositories, powders, and granules. In solid dosage forms, the compositions may be admixed with at least one inert diluent such as sucrose, lactose, or starch, and may additionally comprise lubricating agents, buffering agents, enteric coatings, and other components well known to those skilled in the art.

Actual dosage levels of boron containing agents in the compositions of the invention may be varied so as to obtain amounts of the boron containing agent at the site of target cells, especially tumor cells, effective to obtain the desired therapeutic, prophylactic or diagnostic response. Accordingly, the selected dosage level will depend on the nature and site of the target cells, the desired quantity of boron required at the target cells for effective neutron capture or imaging purposes, the nature and boron content of the boron containing agent employed, the route of administration, and other factors. Generally, a sufficient amount of the boron containing agent is employed to attain a boron content of at least about 1 μg/g of target cell tissue, more preferably at least about 10 μg/g of target cell tissue, and most preferably at least about 20 μg/g of target cell tissue.

The foregoing may be better understood in connection with the following representative examples, which are presented for purposes of illustration and not by way of limitation.

EXAMPLES

Example I

Synthesis of a closo-carboranyl flutamine derivative N-(2'-closo-carboranylacetyl)-3-trifluoromethyl-4-nitroaniline 3

Referring to FIG. 1A, Compound 1 (2-closo-carboranylacetic acid, 0.50 g, 2.5 mmol) was dissolved in thionyl chloride (5 ml, 8.2 g, 68.5 mmol) in an oven dried 25 ml round-bottomed flask fitted with a magnetic stirrer, a condenser, and a drying tube atop the condenser. The mixture was heated at reflux for four hours under a dry nitrogen atmosphere, and then the volatiles were removed under vacuum.

The residue was dissolved in 10 ml of dry ethyl ether (freshly distilled from lithium aluminum hydride) and then added dropwise via syringe to a solution of 5-amino-2-nitrobenzotrifluoride (2, 0.51 g, 2.5 mmol) and 25 ml dry ethyl ether in an oven dried 100 ml round-bottomed flask fitted with a magnetic stirrer, condenser, nitrogen inlet, and ice/water bath. The ice/water bath was then removed and the mixture was heated to reflux for 6 hours, then cooled to room temperature and left stirring overnight.

The precipitated solids (triethylammonium chloride) were filtered off and the solvent was removed under vacuum to obtain a yellow/brown oil which was composed of a 60:40 mixture of 3:2 by $^{19}F$ NMR analysis. Column chromatography (60 A, 230–400 mesh silica gel, 20 cm×2 cm column) using dichloromethane:hexanes (4:1 v/v) afforded 0.301 g (0.77 mmol, 31%) of the desired compound 3, which could be purified farther by recrystallization from toluene:hexanes (1:1 v/v).

Characterization: 19F NMR (ext. ref, freon-11, 0 ppm): δ-64.3 ppm; $^1H$ NMR ($d_6$-acetone/$CDCl_3$): δ10.03 (s, NH), 7.94–7.82 (m, aromatic H), 4.49 (br.s., Carborane CH), 3.26 (s, —$CH_2C$=O), 4.0–0.5 (v. br., $B_{10}H_{10}$); $^{13}C$ NMR ($d_6$-acetone/$CDCl_3$): δ165.4, 143.1, 141.8, 126.7, 125.0, 124.3, 122.4, 118.4, 68.6, 58.7, 43.4.

Example II

Synthesis of a nido-carboranyl flutamine derivative N-(2'0-nido-carboranylacetyl)-3-trifluoromethyl-4-nitroaniline 4

The following synthesis is best understood by reference to FIG. 1A.

The closo-carborane of compound 3 is converted to a nido-carborane following the well known procedure (Varadarajan, A. and Hawthorne, M. F., *Bioconjugate Chem.*, 2:242, 1991). N-(2'-closo-carboranylacetyl)-3-trifluoromethyl-4-nitroaniline 3 (0.250 g, 0.64 mmol, synthesized as in Example I) is dissolved in 10 ml of pyrrolidine in a 25 ml round-bottomed flask fitted with a magnetic stirrer. The mixture is stirred at room temperature for one hour, at which time the solvent is removed under vacuum to afford a brown oil. This residue is dissolved in anhydrous ethanol, and 1 ml of a saturated solution of tetraethylammonium bromide in anhydrous ethanol is added dropwise, resulting in the precipitation of the tetraethyl ammonium salt of compound 4. After recrystallization of this salt from acetone:hexane (1:1 v/v) it is dissolved in a 1:1 mixture of acetonitrile:water (v/v) and loaded into a sodium form ion exchange column (2×20 cm Dowex 50W-A2, pre-equilibrated with 200 ml of a 25:75 mixture (v/v) of acetonitrile:water). The sample is then eluted from the column with 200 ml of a 25:75 mixture (v/v) of acetonitrile:water, collecting 10 ml fractions. The fractions containing the desired product are dried under vacuum to afford the sodium salt 4.

Example III

Synthesis of a nido-carboranyl flutamine derivative N-(4'-carboranylbutanoyl)-3-trifluoromethyl-4-nitroaniline 6

Figure 1B:
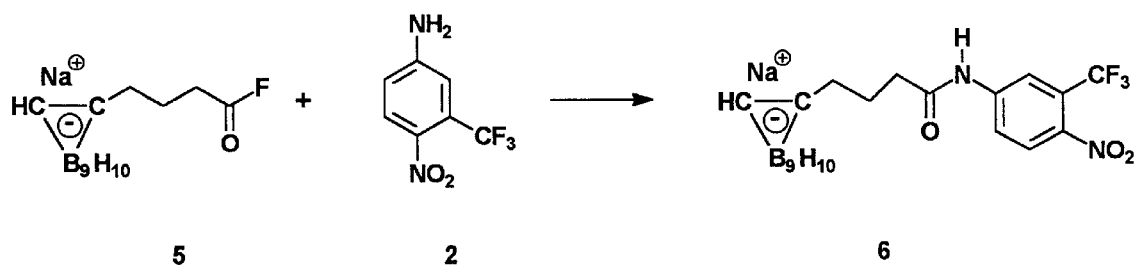
FIG. 1B is a schematic representation of the synthesis pathway for the synthesis of the o-nido-carboranyl flutamnine derivative N-(4'-carboranylbutanoyl)-3-trifluoromethyl-4-nitroaniline 6, as described in Example 3.

The following synthesis is best understood by reference to FIG. 1B.

The 4-nido-carboranylbutanoyl fluoride (5, 1.25 g, 2.5 mmol; Ng, Lai-Ling, UCLA Dissertation, 1993) is added all at once to a solution of 5-amino-2-nitrobenzo-trifluoride (2, 0.51 g, 2.5 mmol), ethyldiisopropyl amine (1.74 ml, 1.29 g, 10 mmol, freshly distilled from calcium hydride under nitrogen), and 25 ml dry ethyl ether in an oven dried 100 ml round-bottomed flask fitted with a magnetic stirrer, nitrogen inlet, and ice/water bath. The ice/water bath is then removed and the resulting mixture stirred at room temperature for 12 hrs.

The reaction mixture is then diluted to 100 ml with diethyl ether and transferred into a 250 ml separatory funnel. This solution is extracted with successive washings with 100 ml of saturated aqueous sodium bicarbonate, 100 ml saturated aqueous ammonium chloride, and 100 ml saturated aqueous sodium chloride. The ether layer is then dried over 10 g of anhydrous magnesium sulfate, filtered, and concentrated under vacuum to afford a brown oil.

The brown oil is then chromatographed (60 A, 230–400 mesh silica gel, 20 cm×2 cm column) using dichloromethane:ethanol (1:0 to 9:1 (v/v) gradient over 500 ml) to yield the pure compound 6 as the triphenylmethyl phosphonium salt. This salt is dissolved in a 1:1 mixture of acetonitrile:water (v/v) and loaded onto a sodium form ion exchange column (2×20 cm Dowex 50W-A2, pre-equilibrated with 200 ml of a 25:75 mixture (v/v) of acetonitrile:water). The sample is then eluted from the column with 200 ml of a 25:75 mixture (v/v) of acetonitrile:water and dried under vacuum to afford the sodium salt 6.

Example IV

Synthesis of a $B_{10}$ flutamine derivative N-(closo-2-$B_{10}H_9$)-N'-(3'-trifluoromethyl-4'-nitroaniline) urea 8

Figure 2A:
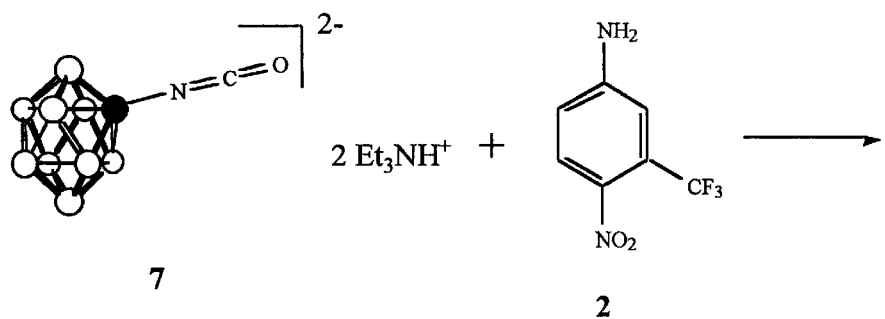
FIG. 2A is a schematic representation of the synthesis pathway for the synthesis of the $B_{10}$ flutamine derivative N-(closo-2-$B_{10}H_9$)-N'-(3'-trifluoromethyl-4'-nitroaniline) urea 8, as described in Example 4.
Figure 2A:
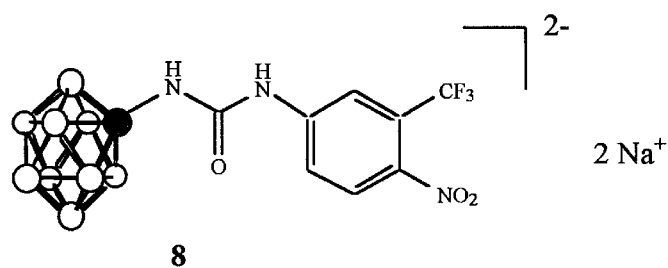

The following synthesis is best understood by reference to FIG. 2A.

Sodium hydride (60% suspension in mineral oil, 0.32 g, 8 mmol) is placed in an oven dried 25 ml round-bottomed flask fitted with a magnetic stirrer, septum, and nitrogen inlet. The gray powder is washed with 5×10 ml of dry hexanes by syringe in order to remove the mineral oil, and then 10 ml of dry tetrahydrofuran is added and the mixture cooled to 0° with an ice/water bath. A solution of 5-amino-2-nitrobenzo-trifluoride (2, 1.53 g, 7.5 mmol) in 5 ml dry tetrahydrofuran is added dropwise by syringe. The ice/water bath is then removed and the resulting solution is stirred at room temperature for four hours, at which time hydrogen evolution has ceased. The mixture is once again placed into the ice/water bath and a solution of compound 7 [closo-2-$B_{10}H_9$]$NCO^{2-}$·[$Et_3NH^+$]$_2$; Shelly, K. et al., *Inorg. Chem.*, 31(13):2889–2892 (1992); 0.91 g, 2.5 mmol) in 5 ml dry tetrahydrofuran is added dropwise over 10 min. The ice/water bath is then removed and the mixture stirred at room temperature for 24 hrs.

The volatiles are then removed under vacuum and the residue dissolved in 2 ml of dichloromethane:ethanol (8:2 v/v). Column chromatography (60 A, 230–400 mesh silica gel, 20 cm×2 cm column) of this solution using dichloromethane:ethanol (8:2 to 1:1 v/v gradient over 500 ml), collecting 10 ml fractions. The excess amine 2 is eluted first, followed by the desired product 8. Fractions containing 8 are pooled and the solvents removed under vacuum. Recrystallization from acetone:pentane (1:1 v/v) will afford the pure compound 8.

Example V

Synthesis of $B_{20}$ flutamine derivative tetrasodium-(apical,apical-1-[2'-$B_{10}H_9$]2-NH-[3"-trifluoromethyl-4"-nitrophenyl]-$B_{10}H_8$10

Figure 2B:
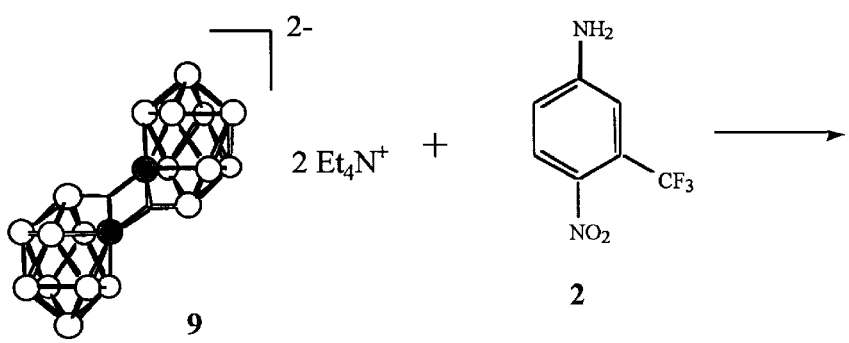
FIG. 2B is a schematic representation of the synthesis pathway for the synthesis of the $B_{20}$ flutamine derivative tetrasodium-(apical, apical-1-[2'-$B_{10}H_9$]-2-NH-[3"-trifluoromethyl-4"-nitrophenyl]-$B_{10}H_8$ 10, as described in Example 5.
Figure 2B:
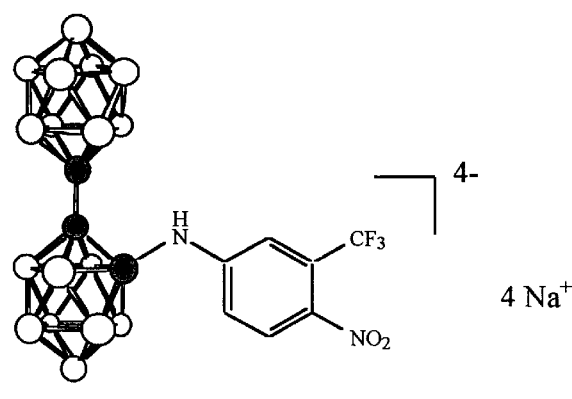

The following synthesis is best understood by reference to FIG. 2B.

Sodium hydride (0.10 g, 60% suspension in mineral oil, 2.5 mmol) is placed in an oven dried 25 ml round-bottomed flask fitted with a magnetic stirrer, septum, and nitrogen inlet. The gray powder is washed with 5×10 ml of dry hexanes by syringe in order to remove the mineral oil, and then 10 ml of dry tetrahydroftiran is added and the mixture is cooled to 0° with an ice/water bath. A solution of 5-amino-2-nitro-benzotrifluoride (2, 0.51 g, 2.5 mmol) in 5 ml dry tetrahydrofuran is added dropwise by syringe. The ice/water bath is then removed and the resulting solution is stirred at room temperature for 4 hrs, at which time hydrogen evolution has ceased. The mixture is once again placed into the ice/water bath and a solution of compound 9 (n-$B_{20}H_{18}^{2-}$·[$Et_4N^+$]$_2$; Hawthorne, M. F. et al., *J. Am. Chem. Soc.*, 85:3704 (1963); Hawthorne, M.F. et al., *J. Am. Chem. Soc.*, 87:4740–4746 (1965); 1.24 g, 2.5 mmol) in 5 ml dry tetrahydrofuran is added all at once. The ice/water bath is then removed and the mixture stirred at room temperature for 24 hrs (Feakes, D. A. et al., *Proc. Natl. Acad Sci. USA*, 91:3029–3033 (1994)).

The volatiles are then removed under vacuum and the residue dissolved in 5 ml anhydrous ethanol. The product is isolated by precipitation using a saturated solution of tetraethylammonium bromide in anhydrous ethanol to afford the crude product as a mixture of apical,equatorial and apical, apical bonded isomers. This solid is dissolved in 10 ml of anhydrous acetonitrile in a dry 25 ml round bottom flask fitted with a magnetic stirrer and an inlet for dry nitrogen, and 0.5 ml of freshly distilled trifluoroacetic acid is added. The resulting solution is stirred at room temperature for 2 hrs, and then the acetonitrile and trifluoroacetic acid are removed under vacuum. Recrystallization of the residue (from acetone:pentane, 8:2 v:v) will afford the pure compound 10 as the tetra-tetraethylammonium salt. This salt is dissolved in a 1:1 mixture of acetonitrile:water (v/v) and loaded onto a sodium form ion exchange column (2×20 cm Dowex 50W-A8, pre-equilibrated with 200 ml of a 25:75 mixture (v/v) of acetonitrile:water). The sample is then eluted from the column with 200 ml of a 25:75 mixture (v/v) of acetonitrile:water, collecting 10 ml fractions. The fractions containing produce are pooled and dried under vacuum to afford the tetrasodium salt 10.

Example VI

Synthesis of a closo-carboranyl oligophosphate trailer flutamine derivative 1-N-(closo-$CB_{10}$-hexylamine)-6-N-(3'-trifluoromethyl-4'-nitroaniline) suberyl diamide 13

Figure 3A:
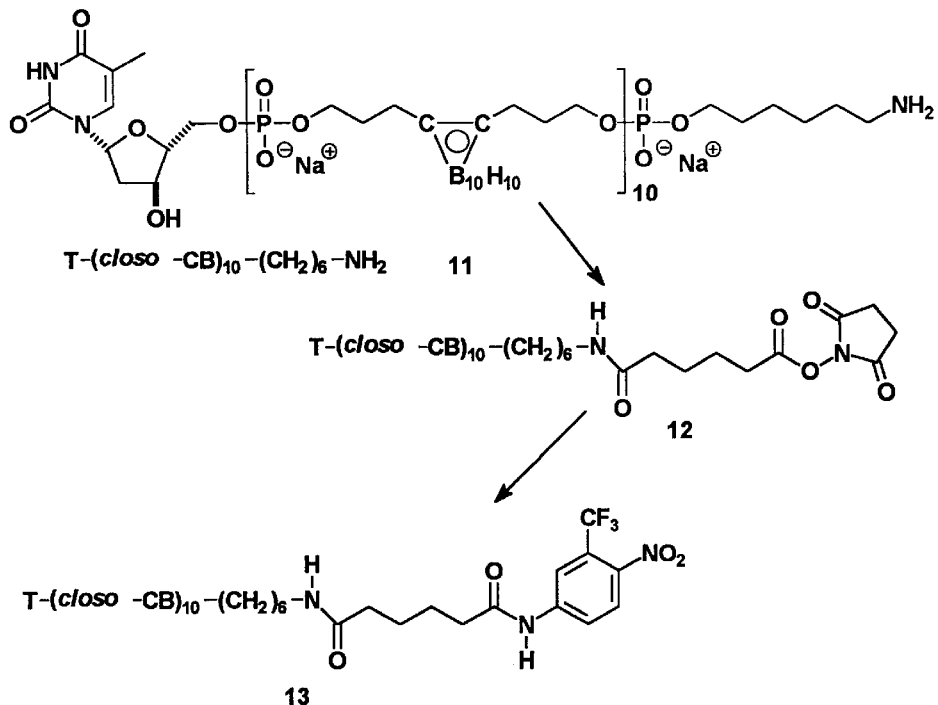
FIG. 3A is a schematic representation of the synthesis pathway for the synthesis of the closo-carboranyl oligophosphate trailer flutamine derivative 1-N-(closo-$CB_{10}$-hexylamine)-6-N-(3'-trifluoromethyl-4'-nitroaniline) suberyl diamide 13, as described in Example 6.

The following synthesis is best understood by reference to FIG. 3A.

The closo-$CB_{10}$-hexylamine (11; Kane, R. R. et al., *J. Am. Chem. Soc.*, 155:8853–8854 (1993); 70 mg, 20 $\mu$mol) is dissolved in 50 mM sodium borate buffer, pH 7.0, to a final concentration of 10 mM (2 ml) in a 10 ml centrifuge tube. A 200 mM solution of disuccinimidyl suberate (DSS; Pierce, Inc.) in ice cold dimethyl-formaide (DMF, 1 ml, 200 $\mu$mol) is prepared in a 1.5 mL microfuge tube, and added to the closo-$CB_{10}$-hexylamine. The centrifuge tube is then gently swirled at room temperature for 2 hrs. A 7 mL portion of ethyl acetate (presaturated with 50 mM sodium borate buffer, pH 7.0) is added to the centrifuge tube and the biphasic mixture is vigorously vortexed for one minute to assure complete mixing. After sitting undisturbed at room temperature for 3 min to allow the layers to completely separate, the ethyl acetate containing the unreacted DSS is decanted from the centrifuge tube. This procedure is repeated four additional times to assure the complete removal of the crosslinker (the desired activated ester, compound 12, is retained in the aqueous layer).

Compound 2 (5-amino-2-nitrobenzotrifluoride, 20 mg, 100 $\mu$mol), is dissolved in 100 $\mu$l of ice cold DMF and added to the aqueous solution of 12 in the centrifuge tube. The resulting milky suspension is vortexed for 6 hrs at room temperature. The entire reaction mixture is then loaded on a PD-10 column (Pharmacia, 10 ml gel bed of Sephadex G-25 pre-equilibrated with 50 ml of Milli-Q water) and the product, conjugate 13, is eluted with 20 ml distilled water, collecting 0.5 ml fractions. Solvent is removed from the product-containing fractions to afford 13 as a white powder.

Example VII

Synthesis of a nido-carboranyl oligophosphate trailer flutamine derivative 1-N-(nido-$CB_{10}$-hexylamine)-6-N-(3'-trifluoromethyl-4'-nitroaniline) suberyl diamide 16

Figure 3B:
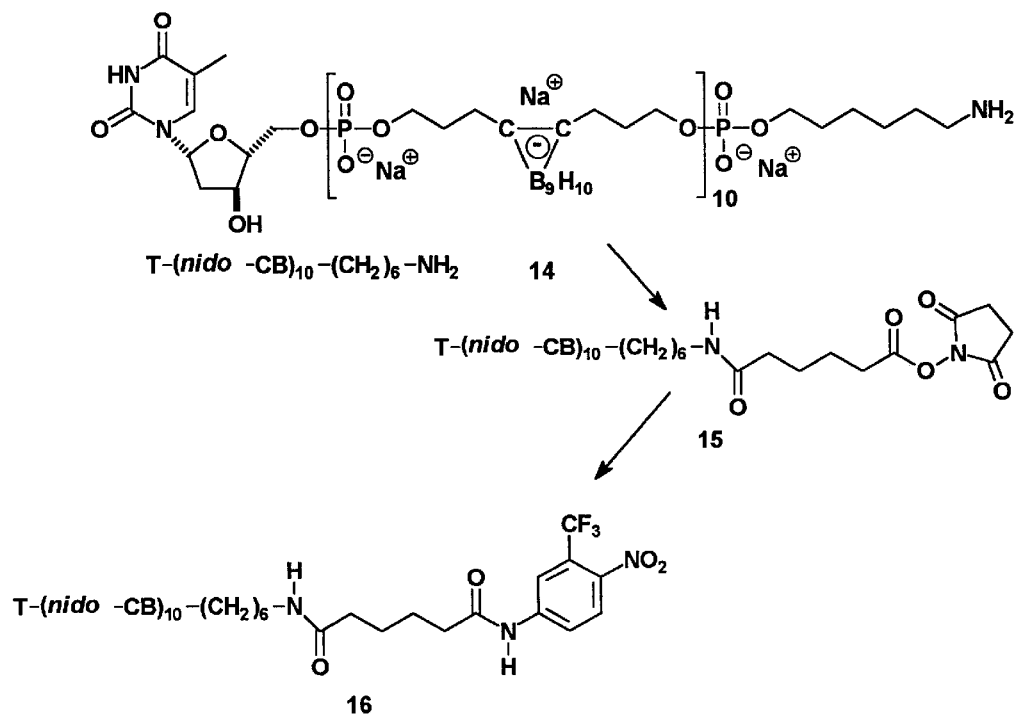
FIG. 3B is a schematic representation of the synthesis pathway for the synthesis of the nido-carboranyl oligophosphate trailer flutamine derivative 1-N-(nido-$CB_{10}$-hexylamine)-6-N-(3'-trifluoromethyl-4'-nitroaniline) suberyl diamide 16, as described in Example 7.

The following synthesis is best understood by reference to FIG. 3B.

The nido-$CB_{10}$-hexylamine (14; Kane, R. R. et al., *J. Am. Chem. Soc.*, 155:8853–8854 (1993); 70 mg, 20 $\mu$mol) is dissolved in 50 mM sodium borate buffer, pH 7.0, to a final concentration of 10 mM (2 ml) in a 10 ml centrifuge tube. A 200 mrM solution of disuccinimidyl suberate (DSS; Pierce, Inc.) in ice cold dimethylformamide (DMF, 1 ml, 200 $\mu$mol) is prepared in a 1.5 mL microfuge tube, and added to the closo-$CB_{10}$-hexylamine. The centrifuge tube is then gently swirled at room temperature for 2 hrs. A 7 mL portion of ethyl acetate (presaturated with 50 mM sodium borate buffer, pH 7.0) is added to the centrifuge tube and the biphasic mixture is vigorously vortexed for 1 min to assure complete mixing. After sitting undisturbed at room temperature for 3 min to allow the layers to completely separate, the ethyl acetate containing the unreacted crosslinker is decanted from the centrifuge tube. This procedure is repeated four additional times to assure the complete removal of the DSS (the desired activated ester, compound 15, is retained in the aqueous layer).

Compound 2 (5-amino-2-nitrobenzotrifluoride, 20 mg, 100 $\mu$mol), is dissolved in 100 $\mu$l of ice cold DMF and added to the aqueous solution of 15 in the centrifuge tube. The resulting milky suspension is vortexed for 6 hrs at room temperature. The entire reaction mixture is then loaded on a PD-10 column (Pharmacia; 10 ml gel bed of Sephadex G-25 pre-equilibrated with 50 ml of Milli-Q water) and the product is eluted with 20 ml distilled water, collecting 0.5 mlA fractions. Solvent is removed from the product-containing fractions to afford 16 as a white powder.

Example VIII

Synthesis of a closo-carboranyl tamoxifen derivative cis-1-(4'-β-(N-2"-closo-carboranylacetyl)-aminoethoxyphenyl)-1,2-diphenylbutene 18

Figure 4A:
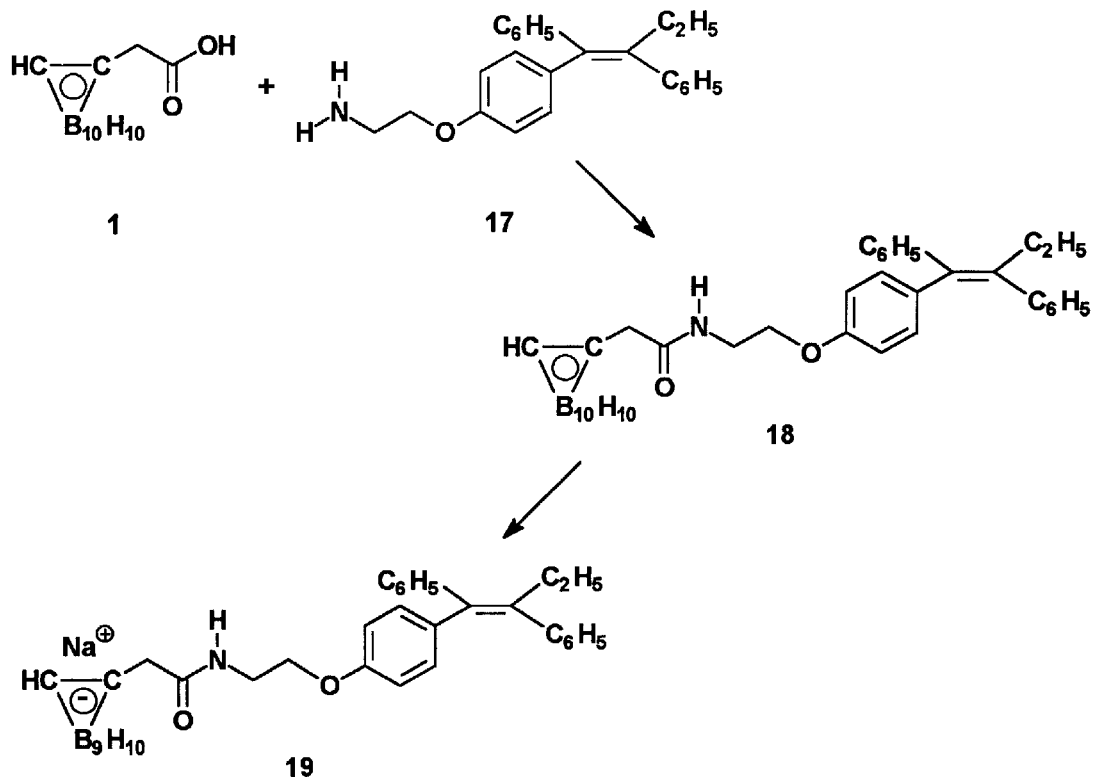
FIG. 4A is a schematic representation of the synthesis pathway for the synthesis of the nido-carboranyl tamoxifen derivative cis-1-(4'-β-(N-2"-nido-carboranylacetyl)-aminoethoxyphenyl)-1,2-diphenylbutene 19, as described in Examples 8 and 9.

The following synthesis is best understood by reference to FIG. 4A.

Sodium hydride (60% suspension in mineral oil, 0.32 g, 8 mmol) is placed in an oven dried 25 ml round-bottomed flask fitted with a magnetic stirrer, septum, and nitrogen inlet. The gray powder is washed with 5×10 ml of dry hexanes by syringe in order to remove the mineral oil, and then 10 ml of dry tetrahydrofuran is added and the mixture is cooled to 0° with an ice/water bath. A solution of cis-1-(4'-β-amino-ethoxyphenyl)-1,2-diphenylbutene (O. Stanciuc and A. T. Balaban, "Reaction of Pyrillium Salts with Nucleophiles. 23: Triarylethylene Derivatives Containing an Oxyalkyleneamino or Oxyalkylene-N-pyridinium Side Chain," *J. Pharm. Sci.*, 82(9):927–933, 17, 2.68 g, 7.5 mmol) in 5 ml dry tetrahydrofuran is added dropwise by syringe. The ice/water bath is then removed and the resulting solution is stirred at room temperature for 4 hrs, at which time hydrogen evolution has ceased .

Compound 1 (2-closo-carboranylacetic acid, 0.50 g, 2.5 mmol) is dissolved in thionyl chloride (5 ml, 8.2 g, 68.5 mmol) in a second oven dried 25 ml round-bottomed flask fitted with a magnetic stirrer, a condenser, and a drying tube atop the condenser. The mixture is heated at reflux for 4 hrs under a dry nitrogen atmosphere, and then the volatiles are removed under vacuum. This residue is dissolved in 10 ml of dry ethyl ether (freshly distilled from lithium aluminum hydride) and then added dropwise over 10 min to the sodium salt of cis-1-(4'-β-aminoethoxyphenyl)-1,2-diphenylbutene (prepared above) which has been cooled to 0° by immersing the flask in an ice/water bath. The ice/water bath is then removed and the mixture is heated to reflux for 6 hrs, then cooled to room temperature and left stirring overnight.

The solvent is removed under vacuum to obtain a yellow/brown oil. Column chromatography (60 A, 230–400 mesh silica gel, 20 cm×2 cm column) using dichloromethane:hexanes (4:1 v/v, 500 ml) affords compound 18, which can be purified further by recrystallization from toluene:hexanes (1:1 v/v).

Example IX

Synthesis of a nido-carboranyl tamoxifen derivative cis-1-(4'-β-(N-2"-nido-carboranylacetyl)-aminoethoxyphenyl)-1,2-diphenylbutene 19

The following synthesis is best understood by reference to FIG. 4A.

The closo-carborane of compound 18 is converted to a nido-carborane following the well known procedure (Varadarajan, A. and Hawthorne, M. F., *Bioconjugate Chem.*, 2:242 (1991)). Cis-1-(4'-β-(N-2"-closo-carboranylacetyl)-aminoethoxyphenyl)-1,2-diphenylbutene 18 (0.347 g, 0.64 mmol, synthesized as in Example VIII) is dissolved in 10 ml of pyrrolidine in a 25 ml round-bottomed flask fitted with a magnetic stirrer. The mixture is stirred at room temperature for 1 hr, at which time the solvent is removed under vacuum to afford a brown oil. This residue is dissolved in anhydrous ethanol, and 1 ml of a saturated solution of tetraethyl-ammonium bromide in anhydrous ethanol is added dropwise, resulting in the precipitation of the tetraethyl ammonium salt of compound 19. After recrystallization of this salt from acetone:hexane (1:1 v/v) it is dissolved in a 1:1 mixture of acetonitrile:water (v/v) and loaded onto a sodium form ion exchange column (2×20 cm Dowex 50W-A2, pre-equilibrated with 200 ml of a 25:75 mixture (v/v) of acetonitrile:water). The sample is then eluted from the column with 200 ml of a 25:75 mixture (v/v) of acetonitrile:water, collecting 10 ml fractions. The fractions containing the desired product are dried under vacuum to afford the sodium salt 19.

Example X

Synthesis of a nido-carboranyl tamoxifen derivative cis-1-(4'-β-(N-4"-nido-carboranylbutanoyl)-aminoethoxyphenyl)-1,2-diphenylbutene 20

Figure 4B:
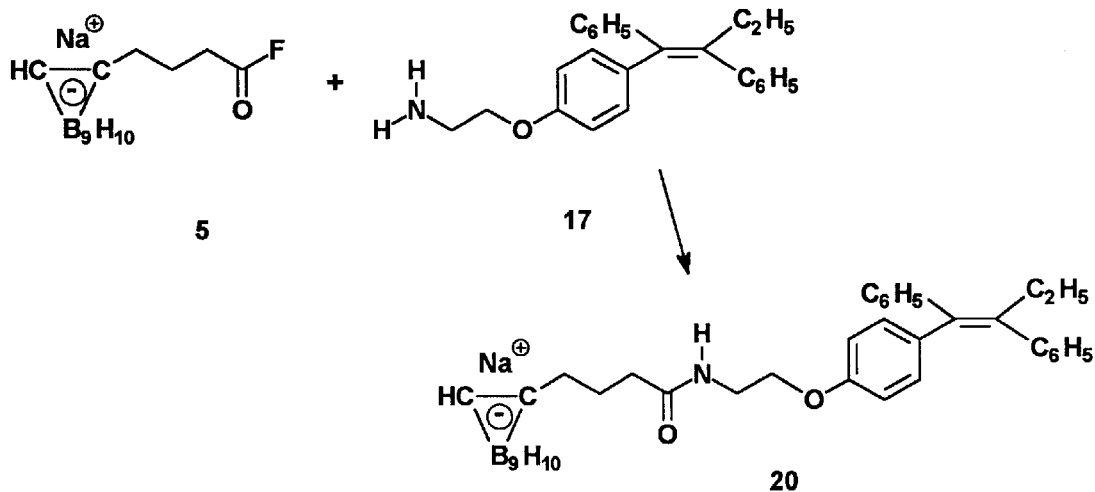
FIG. 4B is a schematic representation of the synthesis pathway for the synthesis of the nido-carboranyl tamoxifen derivative cis-1-(4'-β-(N-4"-nido-carboranylacetyl)-aminoethoxyphenyl)-1,2-diphenylbutene 20, as described in Example 10.

The following synthesis is best understood by reference to FIG. 4B.

Sodium hydride (60% suspension in mineral oil, 0.32 g, 8 mmol) is placed in an oven dried 25 ml round-bottomed flask fitted with a magnetic stirrer, septum, and nitrogen inlet. The gray powder is washed with 5×10 ml of dry hexanes by syringe in order to remove the mineral oil, and then 10 ml of dry tetrahydrofuran is added and the mixture is cooled to 0° with an ice/water bath. A solution of cis-1-(4'-β-aminoethoxyphenyl)-1,2-diphenylbutene (17, 2.68 g, 7.5 mmol) in 5 ml dry tetrahydrofuran is added dropwise by syringe. The ice/water bath is then removed and the resulting solution is stirred at room temperature for 4 hrs, at which time hydrogen evolution has ceased. The mixture is once again placed into the ice/water bath and a solution of compound 5, 4-nido-carboranylbutanoyl fluoride (5, 1.25 g, 2.5 mmol; Ng, Lai-Ling, UCLA Dissertation, 1993), in 5 ml dry tetrahydrofuran is added dropwise over 10 min. The ice/water bath is then removed and the mixture stirred at room temperature for 24 hrs.

The reaction mixture is then diluted to 100 ml with diethyl ether and transferred into a 250 ml separatory funnel. This solution is extracted with successive washings with 100 ml of saturated aqueous sodium bicarbonate, 100 ml saturated aqueous ammonium chloride, and 100 ml saturated aqueous sodium chloride. The ether layer is then dried over 10 g of anhydrous magnesium sulfate, filtered, and concentrated under vacuum to afford a brown oil.

The brown oil is then chromatographed (60 A, 230–400 mesh silica gel, 20 cm×2 cm column) using dichloromethane:ethanol (1:0 to 9:1 (v/v) gradient over 500 ml) to yield the pure compound 20 as a triphenylmethyl phosphonium salt. This salt is dissolved in a 1:1 mixture of acetonitrile:water (v/v) and loaded onto a sodium form ion exchange column (2×20 cm Dowex 50W-A2, pre-equilibrated with 200 ml of a 25:75 mixture (v/v) of acetonitrile:water). The sample is then eluted from the column with 200 ml of a 25:75 mixture (v/v) of acetonitrile:water and dried under vacuum to afford the sodium salt 20.

Example XI

Synthesis of a $B_{10}$ tamoxifen derivative $Na_2$(N-[closo-2-$B_{10}H_9$]-N'-[cis-1-(4'-β-aminoethoxyphenyl)-1,2-diphenylbutene]urea)21

Figure 5A:
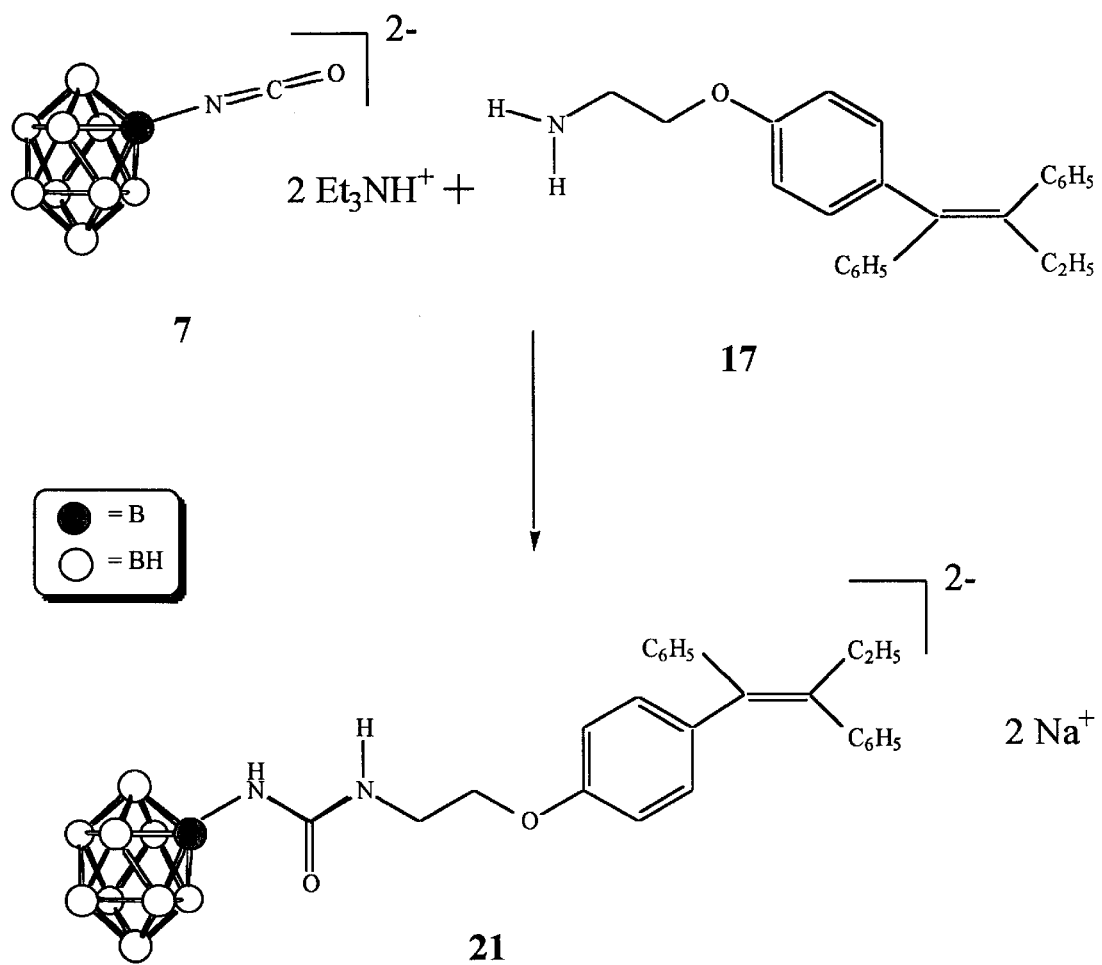
FIG. 5A is a schematic representation of the synthesis pathway for the synthesis of the $B_{10}$ tamoxifen derivative $Na_2(N-[closo-2-B_{10}H_9]-N'[cis-1-(4'-β-aminoethoxyphenyl)-1,2-diphenylbutene]urea)$ 21, as described in Example 11.

The following synthesis is best understood by reference to FIG. 5A.

Sodium hydride (60% suspension in mineral oil, 0.32 g, 8 mmol) is placed in an oven dried 25 ml round-bottomed flask fitted with a magnetic stirrer, septum, and nitrogen inlet. The gray powder is washed with 5×10 ml of dry hexanes by syringe in order to remove the mineral oil, and then 10 ml of dry tetrahydrofuran is added and the mixture is cooled to 0° with an ice/water bath. A solution of cis-1-(4'-β-aminoethoxyphenyl)-1,2-diphenylbutene (17, 2.68 g, 7.5 mmol) in 5 ml dry tetrahydrofuran is added dropwise by syringe. The ice/water bath is then removed and the resulting solution is stirred at room temperature for 4 hrs, at which time hydrogen evolution has ceased. The mixture is once again placed into the ice/water bath and a solution of compound 7 (closo-2-$B_{10}H_9NCO^{2-}$·[$Et_3NH^+$]$_2$; Shelly K. et al., *Inorg. Chem.*, 31(13):2889–2892 (1992); 0.91 g, 2.5 mmol) in 5 ml dry tetrahydrofuran is added dropwise over 10 min. The ice/water bath is then removed and the mixture stirred at room temperature for 24 hrs.

The volatiles are then removed under vacuum and the residue dissolved in 2 ml of dichloromethane:ethanol (8:2 v/v). Column chromatography (60 A, 230–400 mesh silica gel, 20 cm×2 cm column) of this solution using dichloromethane:ethanol (8:2 to 1:1 v/v gradient over 500 ml), collecting 10 ml fractions. The excess amine 17 is eluted first, followed by the desired product. Fractions containing 21 are pooled and the solvents removed under vacuum. Recrystallization from acetone:pentane (1:1 v/v) will afford the pure compound 21.

Example XI

Synthesis of a $B_{20}$ tamoxifen derivative $Na_4$(apical, apical-1-[2'-$B_{10}H_9$]-2-[N-cis-1-(4'-β-aminoethoxyphenyl)-1,2-diphenylbutene]-$B_{10}H_8$)22

Figure 5B:
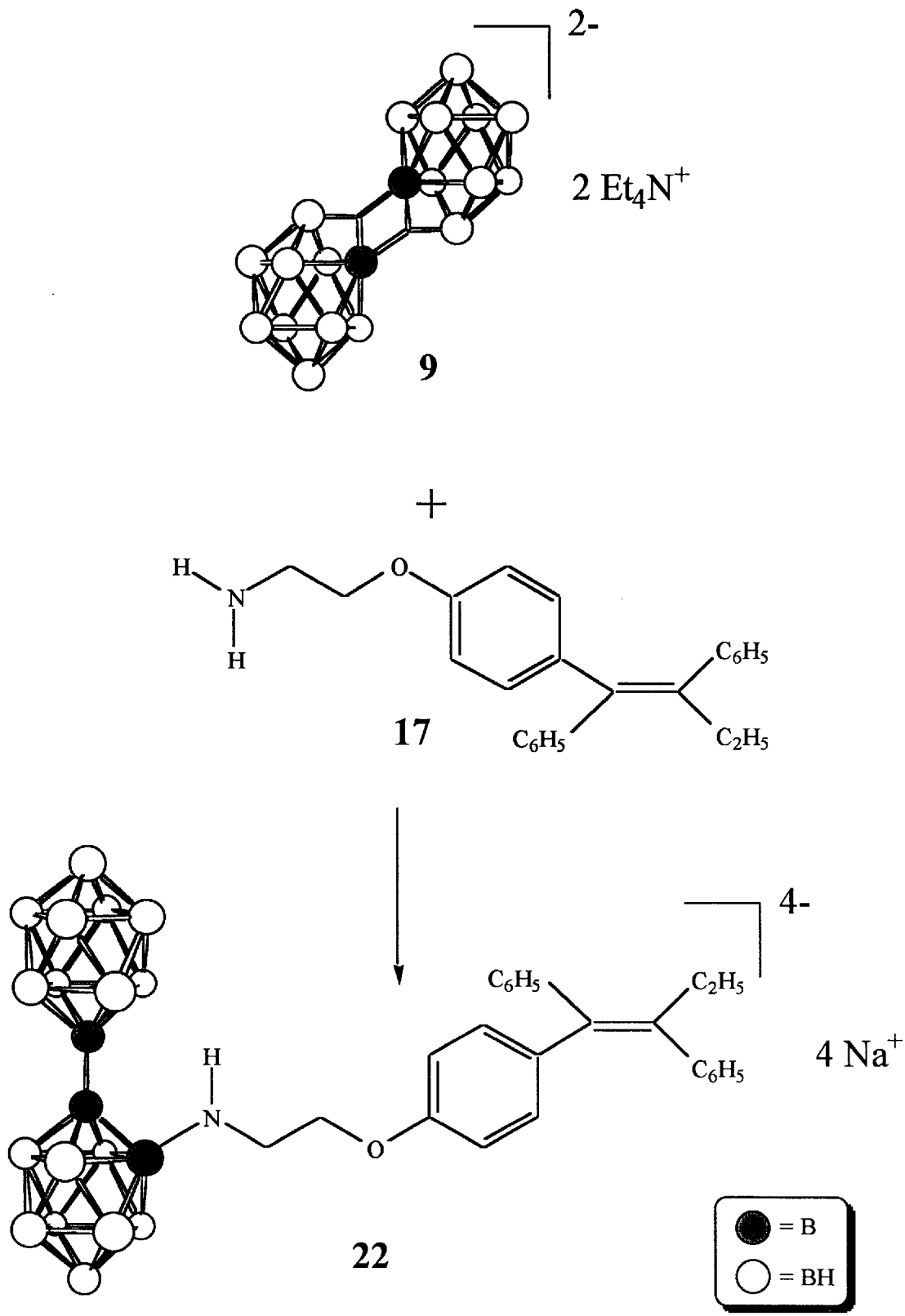
FIG. 5B is a schematic representation of the synthesis pathway for the synthesis of the $B_{20}$ tamoxifen derivative $Na_4$(apical,apical-1-[2'-$B_{10}H_9$]-2-[N-cis-1-(4'-β-aminoethoxyphenyl)-1,2-diphenylbutene]-$B_{10}H_8$) 22, as described in Example 12.

The following synthesis is best understood by reference to FIG. 5B.

Sodium hydride (0.10 g, 60% suspension in mineral oil, 2.5 mmol) is placed in an oven dried 25 ml round-bottomed flask fitted with a magnetic stirrer, septum, and nitrogen inlet. The gray powder is washed with 5×10 ml of dry hexanes by syringe in order to remove the mineral oil, and then 10 ml of dry tetrahydrofuran is added and the mixture is cooled to 0° with an ice/water bath. A solution of cis-1-(4'-β-aminoethoxyphenyl)-1,2-diphenylbutene (17, 0.89 g, 2.5 mmol) in 5 ml dry tetrahydrofuran is added dropwise by syringe. The ice/water bath is then removed and the resulting solution is stirred at room temperature for 4 hrs, at which time hydrogen evolution has ceased. The mixture is once again placed into the ice/water bath and a solution of compound 9 (n-$B_{20}H_{18}^{2-}$·[$Et_4N^+$]$_2$; Hawthorne, M. F. et al., *J. Am. Chem. Soc.*, 85:3704 (1963); Hawthorne, M. F. et al., *J. Am. Chem. Soc.*, 87:4740–4746 (1965); 1.24 g, 2.5 mmol) in 5 ml dry tetrahydrofuran is added all at once. The ice/water bath is then removed and the mixture stirred at room temperature for 24 hrs (Feakes, D. A. et al., *Proc. Natl. Acad Sci. USA*, 91:3029–3033 (1994)).

The volatiles are then removed under vacuum and the residue dissolved in 5 ml anhydrous ethanol. The product is isolated by precipitation using a saturated solution of tetraethylammonium bromide in anhydrous ethanol to afford the crude product as a mixture of apical,equatorial and apical, apical bonded isomers. This solid is dissolved in 10 ml of anhydrous acetonitrile in a dry 25 ml round bottom flask fitted with a magnetic stirrer and an inlet for dry nitrogen, and 0.5 ml of freshly distilled trifluoroacetic acid is added. The resulting solution is stirred at room temperature for 2 hrs, and then the acetonitrile and trifluoroacetic acid are removed under vacuum. Recrystallization of the residue (from acetone:pentane, 8:2 v:v) will afford the pure compound 22 as the tetra-tetraethylammonium salt. This salt is dissolved in a 1:1 mixture of acetonitrile:water (v/v) and loaded onto a sodium form ion exchange column (2×20 cm Dowex 50W-A8, pre-equilibrated with 200 ml of a 25:75 mixture (v/v) of acetonitrile:water). The sample is then eluted from the column with 200 ml of a 25:75 mixture (v/v) of acetonitrile:water, collecting 10 ml fractions. The fractions containing product are pooled and dried under vacuum to afford the tetra-sodium salt 22.

Example XIII

Synthesis of a closo-carboranyl oligophosphate trailer tamoxifen derivative $N_1$-(closo-CB10-hexylamine)-$N_6$-(cis-1-[4'-β-aminoethoxyphenyl]-1, 2-diphenylbutene)-suberyl diamide 23

Figure 6:
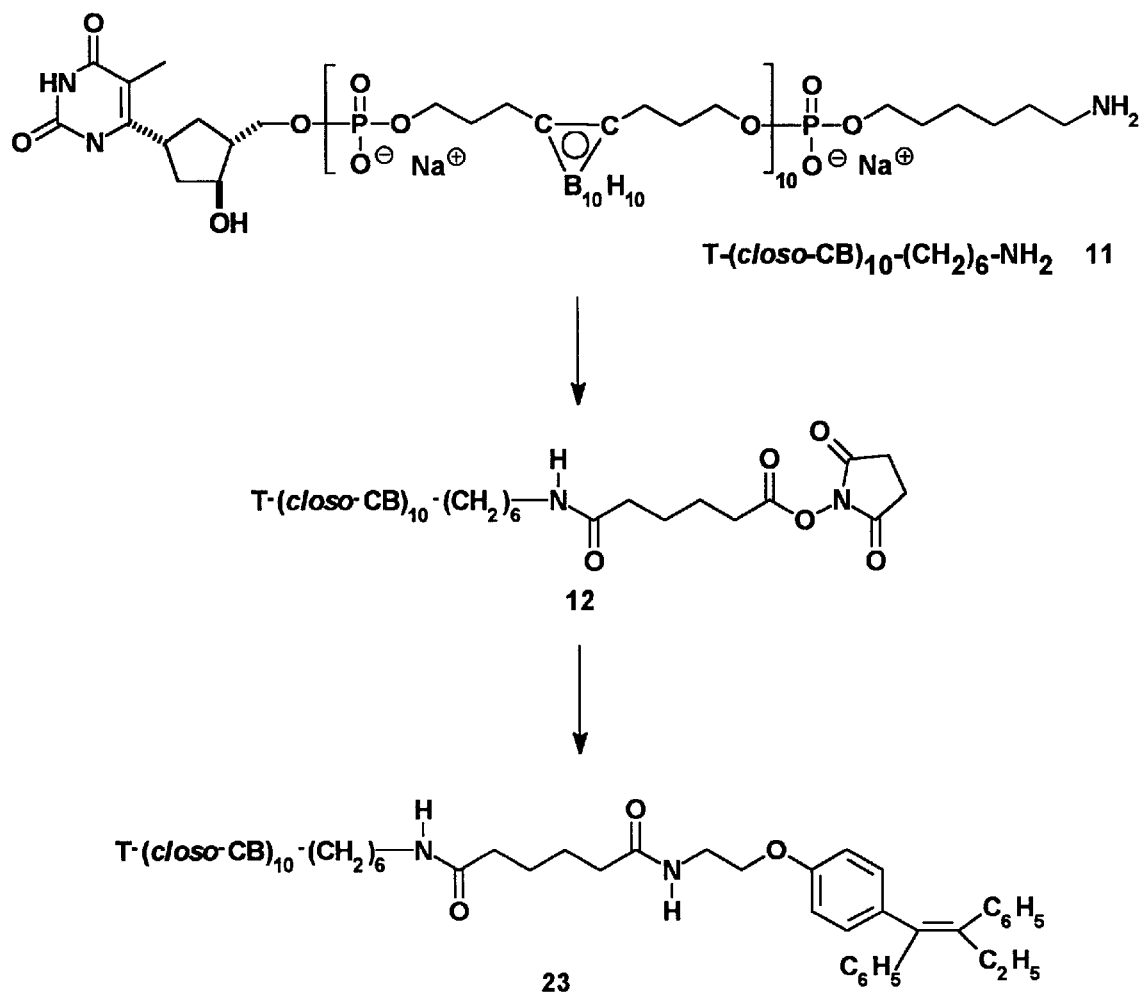
FIG. 6 is a schematic representation of the synthesis pathway for the synthesis of the closo-carboranyl oligophosphate trailer tamoxifen derivative $N_1$-(closo-CB10-hexylamine)-$N_6$-(cis-1-[4'-β-aminoethoxyphenyl]-1,2-diphenylbutene)-suberyl diamide 23, as described in Example 13.

The following synthesis is best understood by reference to FIG. 6.

The closo-$CB_{10}$-hexylamine (11; Kane, R. R. et al., *J. Am. Chem. Soc.*, 155:8853–8854 (1993); 70 mg, 20 µmol) is dissolved in 50 mM sodium borate buffer, pH 7.0, to a final concentration of 10 mM (2 ml) in a 10 ml centrifuge tube. A 200 mM solution of disuccinimidyl suberate (DSS, Pierce Inc.) in ice cold dimethyl-formamide (DMF, 1 ml, 200 µmol) is prepared in a 1.5 mL microfuge tube, and added to the closo-$CB_{10}$-hexylamine. The centrifuge tube is then gently swirled at room temperature for 2 hrs. A 7 mL portion of ethyl acetate (presaturated with 50 mM sodium borate buffer, pH 7.0) is added to the centrifuge tube and the biphasic mixture is vigorously vortexed for one minute to assure complete mixing. After sitting undisturbed at room temperature for 3 minutes to allow the layers to completely separate, the ethyl acetate containing the unreacted DSS is decanted from the centrifuge tube. This procedure is repeated four additional times to assure the complete removal of the crosslinker (the desired activated ester, compound 12, is retained in the aqueous layer).

Compound 17, cis-1-(4'-β-aminoethoxyphenyl)-1,2-diphenylbutene, 36 mg, 100 µmol), is dissolved in 100 µl of ice cold DMF and added to the aqueous solution of 12 in the centrifuge tube. The resulting milky suspension of vortexed for 6 hrs at room temperature. The entire reaction mixture is then loaded on a PD-10 column (Pharmacia, 10 ml gel bed of Sephadex G-25 pre-equilibrated with 50 ml of Milli-Q water) and the product, conjugate 23, is eluted with 20 ml distilled water, collecting 0.5 ml fractions. Solvent is removed from the product-containing fractions to afford 23 as a white powder.

Example XIV

Synthesis of a nido-carboranyl oligophosphate trailer tamoxifen derivative $N_1$-(nido -CB10-hexylamine)-$N_6$-(cis-1-[4'-β-aminoethoxyphenyl]-1, 2-diphenylbutene)-suberyl diamide 24

Figure 7:
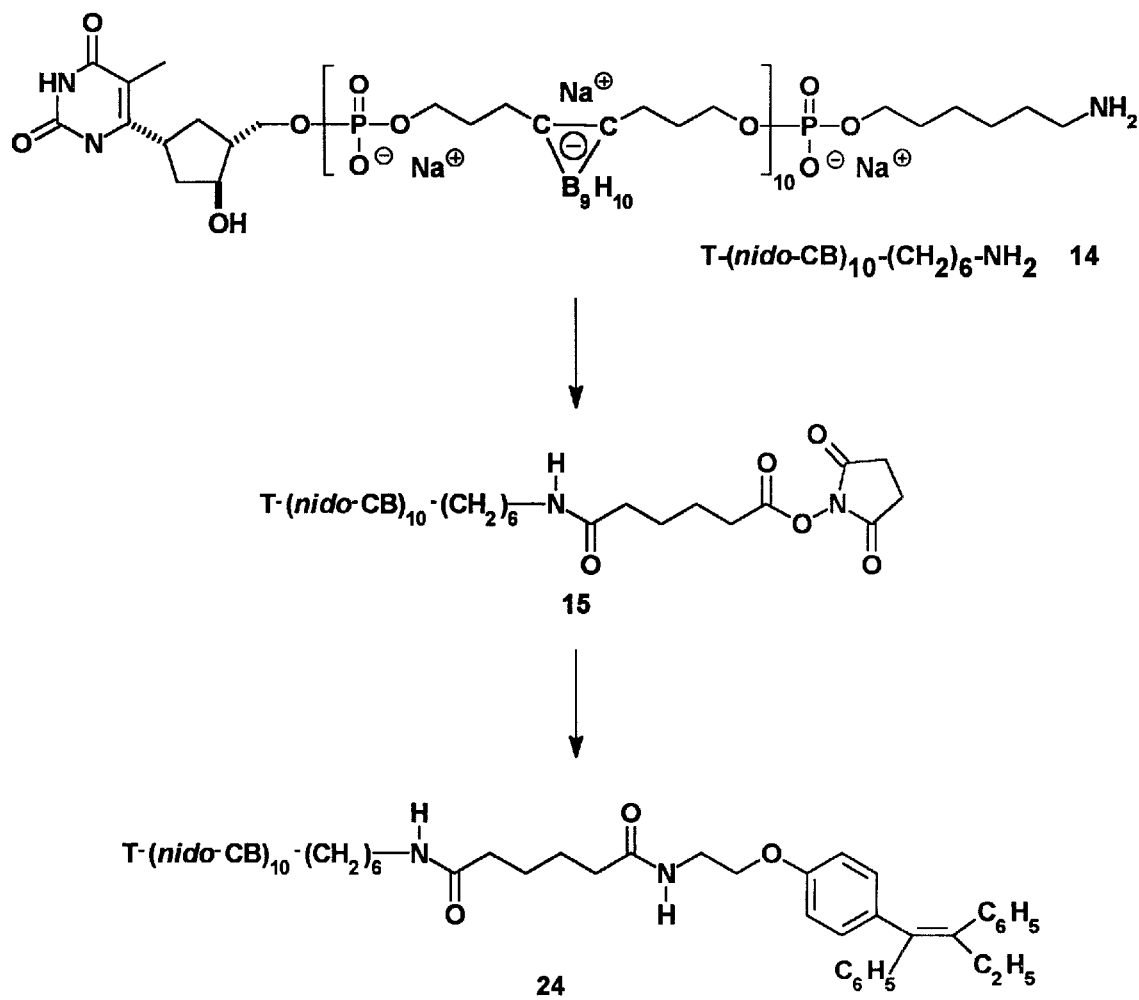
FIG. 7 is a schematic representation of the synthesis pathway for the synthesis of the nido-carboranyl oligophosphate trailer tamoxifen derivative $N_1$-(nido-CB10-hexylamine)-$N_6$-(cis-1-[4'-β-aminoethoxyphenyl]-1,2-diphenylbutene)-suberyl diamide 24 as described in Example 14.

The following synthesis is best understood by reference to FIG. 7.

The nido-$CB_{10}$-hexylamine (14; Kane, R. R. et al., *J. Am. Chem. Soc.*, 155:8853–8854 (1993); 70 mg, 20 µmol) is dissolved in 50 mM sodium borate buffer, pH 7.0, to a final concentration of 10 mM (2 ml) in a 10 ml centrifuge tube. A 200 mM solution of disuccinimidyl suberate (DSS; Pierce, Inc.) in ice cold dimethyl-formamide (DMF, 1 ml, 200 µmol) is prepared in a 1.5 mL microfuge tube, and added to the closo-$CB_{10}$-hexylamine. The centrifuge tube is then gently swirled at room temperature for 2 hrs. A 7 mL portion of ethyl acetate (presaturated with 50 mM sodium borate buffer, pH 7.0) is added to the centrifuge tube and the biphasic mixture is vigorously vortexed for 1 min to assure complete mixing. After sitting undisturbed at room temperature for 3 min to allow the layers to completely separate, the ethyl acetate containing the unreacted crosslinker is decanted from the centrifuge tube. This procedure is repeated four additional times to assure the complete removal of the DSS (the desired activated ester, compound 15, is retained in the aqueous layer).

Compound 17 cis-1-(4'-β-aminoethoxyphenyl)-1,2-diphenylbutene, 36 mg, 100 µmol), is dissolved in 100 µl of ice cold DMF and added to the aqueous solution of 15 in the centrifuge tube. The resulting milky suspension is vortexed for 6 hrs at room temperature. The entire reaction mixture is then loaded on a PD-10 column (Pharmacia; 10 ml gel bed of Sephadex G-25 pre-equilibrated with 50 ml of Milli-Q water) and the product is eluted with 20 ml distilled water, collecting 0.5 ml fractions. Solvent is removed from the product-containing fractions to afford 24 as a white powder.

Example XV

Receptor Binding

The specificity of the compound of Example I for androgen receptors was determined in a standard androgen receptor assay. See Schilling et al., "The Use of Radioactive 7α, 17α-dimethyl-19-nortestosterone (Mibolerone) in the Assay of Androgen Receptors," *The Prostate*, 5:581–588 (1984); Traish et al., "Binding of 7α, 17-α-dimethyl-19-nortestosterone (Mibolerone) to Androgen and Progesterone Receptors in Human and Animal Tissues," *Endocrinology* 118:1327–1333 (1986). Cytosol prepared from rat ventral prostate was incubated with 2 nM [$^3$H] mibolerone (DMNT) for 18 hrs at 4° C. The reaction mixture was then incubated with a hydroxy apatite slurry containing various concentrations of N-(2'-closo-carboranylacetyl)-3-trifluoromethyl-4-nitroaniline 3 from Example 1, as shown below. The mixtures were then filtered through glass fiber filters, washed three times and counted to determine the inhibition of mibolerone binding to the androgen receptors. The results are shown in the following Table 1:

TABLE 1

[³H] Mibolerone Binding Inhibiton

| Boron Agent Concentration ($\mu$M) | % Inhibition |
|---|---|
| 100 | 85 |
| 10 | 29 |
| 1 | 7 |
| 0.1 | 3 |
| 0.01 | 3 |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of targeting boron to cells that contain intracellular receptors comprising contacting the cells with a conjugate comprising a boron containing moiety, wherein the boron containing moiety contains at least nine $^{10}$B atoms, conjugated to a ligand having binding specificity for it least one intracellular receptor of the cells.

2. A method of killing intracellular receptor containing cells comprising contacting the cells with a boron neutron capture agent comprising a $^{10}$B containing moiety, wherein the $^{10}$B containing moiety contains at least nine $^{10}$B atoms, conjugated to a ligand having binding specificity for at least one intracellular receptor of the cells, and then irradiating the cells with neutrons.

3. The method of claim 1 wherein the cells are tumor cells.

4. The method of claim 2 wherein the cells are metastatic breast cancer cells and the ligand comprises a $^{10}$B containing moiety conjugated to ligand having binding specificity for estrogen receptors.

5. The method of claim 4 wherein the ligand comprises a $^{10}$B containing moiety conjugated to tamoxifen.

6. The method of claim 2 wherein the cells are prostate cancer cells and the ligand comprises a $^{10}$B containing moiety conjugated to ligand having binding specificity for androgen receptors.

7. The method of claim 6 wherein the ligand comprises a $^{10}$B containing moiety conjugated to a 4'-substituted or a 3',4'-disubstituted anilide residue.

8. The method of claim 7 wherein the anilide residue is 4'-nitro-3'-trifluoromethyl-isobutyranilide residue.

9. The method of claim 6 wherein the ligand comprises a $^{10}$B containing moiety conjugated to a cyproterone acetate residue.

10. The method of claim 2 wherein the cells are leukemia cells and the ligand comprises a $^{10}$B containing moiety conjugated to ligand having binding specificity for glucocorticoid receptors.

11. The method of claim 2 wherein the cells are renal carcinoma cells and the ligand comprises a $^{10}$B containing moiety conjugated to ligand having binding specificity for progesterone receptors, androgen receptors or glucocorticoid receptors.

12. The method of claim 2 wherein the cells are endometrial cancer cells and the ligand comprises a $^{10}$B containing moiety conjugated to ligand having binding specificity for estrogen receptors or progesterone receptors.

13. The method of claim 2 wherein the cells are ovarian carcinoma cells and the ligand comprises a $^{10}$B containing moiety conjugated to ligand having binding specificity for estrogen receptors or progesterone receptors.

14. The method of claim 2 wherein the cells are carcinoma cells of the cervix, vagina or vulva and the ligand comprises a $^{10}$B containing moiety conjugated to ligand having binding specificity for estrogen receptors or progesterone receptors.

15. The method of claim 2 wherein the $^{10}$B containing moiety comprises at least one carborane residue.

16. The method of claim 2 wherein the cells are irradiated with thermal neutrons.

17. The method of claim 2 wherein the cells are irradiated with epithermal neutrons.

18. The method of claim 2 wherein the cells are irradiated with fast neutrons.

19. A method of killing intracellular receptor containing cells comprising contacting the cells with a boron neutron capture agent comprising a $^{10}$B containing moiety, wherein the $^{10}$B containing moiety contains more than one $^{10}$B atom, conjugated to a ligand having binding specificity for at least one intracellular receptor of the cells, and then irradiating the cells with neutrons.

20. A method of killing intracellular receptor containing cells comprising contacting the cells with a boron neutron capture agent comprising a $^{10}$B containing moiety, wherein the $^{10}$B containing moiety comprises at least one carborane residue, conjugated to a ligand having binding specificity for at least one intracellular receptor of the cells, and irradiating the cells with neutrons.

21. The method of claim 20 wherein the $^{10}$B containing moiety is selected from the class of compounds having the following formula:

$$R_1-O\left(\begin{array}{c}O\\\|\\P\\|\\O^-M^+\end{array}-O-(CH_2)_{\overline{m}}-C\underset{B_9H_{10}^-\ M^+}{\overset{O}{\diagdown\diagup}}C-(CH_2)_{\overline{m}}-O\right)_n\begin{array}{c}O\\\|\\P\\|\\O^-M^+\end{array}-O-(CH_2)_{\overline{m}}-C\underset{B_9H_{10}^-\ M^+}{\overset{O}{\diagdown\diagup}}C-(CH_2)_{\overline{m}}-R_2$$

wherein $M^+$ is selected from the group consisting of an alkali metal cations and tetra alkyl ammonium;

$R_1$ is a group selected from the categories of compounds suitable for linking to a ligand and targeting moieties;

$R_2$ is a group selected from the categories of compounds suitable for linking to a ligand and targeting moieties;

m is an integer from 1 to 10; and n is an integer from 2 to 150.

22. A method of killing intracellular receptor containing cells comprising contacting the cells with a boron neutron capture agent comprising a $^{10}$B containing moiety, wherein the $^{10}$B containing moiety comprises at least one carboranyl residue, conjugated to a ligand having binding specificity for at least one intracellular receptor of the cells, and irradiating the cells with neutrons.

23. The method of claim 22 wherein the $^{10}$B containing moiety is selected from the class of compounds having the following formula:

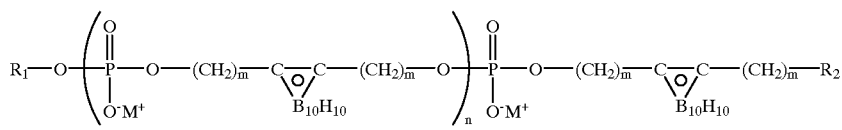

wherein M⁺ is selected from the group consisting of an alkali metal cations and tetra alkyl ammonium;

R₁ is a group selected from the categories of compounds suitable for linking to a ligand and targeting moieties;

R₂ is a group selected from the categories of compounds suitable for linking to a ligand and targeting moieties;

m is an integer from 1 to 10; and n is an integer from 2 to 150.

* * * * *